United States Patent [19]

Keavy et al.

[11] Patent Number: 5,753,709
[45] Date of Patent: May 19, 1998

[54] N-ACYL-2 ARYL CYCLOPROPYLMETHYLAMINE DERIVATIVES AS MELATONERGICS

[75] Inventors: Daniel J. Keavy, Middletown; Michael F. Parker, Somers; Ronald J. Mattson, Meriden; Graham Johnson, Madison, all of Conn.

[73] Assignee: Bristol-Myers Squibb Company, Princeton, N.J.

[21] Appl. No.: 644,087

[22] Filed: May 9, 1996

Related U.S. Application Data

[63] Continuation-in-part of Ser. No. 486,633, Jun. 7, 1995.

[51] Int. Cl.[6] .................... A61K 31/16; C07C 233/05
[52] U.S. Cl. .................... 514/630; 514/520; 514/624; 514/625; 514/627; 514/628; 514/616; 558/414; 564/189; 564/190; 564/207; 564/209; 564/210; 564/211; 564/215; 564/217; 564/218; 564/155; 564/158

[58] Field of Search .................... 564/189, 190, 564/207, 209, 210, 211, 215, 217, 218, 155, 158; 514/624, 625, 627, 628, 630, 520, 616; 558/414

[56] References Cited

U.S. PATENT DOCUMENTS 5,521,212  5/1996  Ikeda et al. .................... 514/428

FOREIGN PATENT DOCUMENTS

WO 95/22521  2/1994  Japan.

OTHER PUBLICATIONS

Bonnaud et.al., J. Med. Chem., vol. 30, 318–325, 1987.

*Primary Examiner*—Shailendra Kumar
*Attorney, Agent, or Firm*—Aldo A. Algieri

[57] ABSTRACT

Certain N-acyl 2-aryl cyclopropylmethylamine derivatives are useful as melatonergic agents.

19 Claims, No Drawings

N-ACYL-2 ARYL CYCLOPROPYLMETHYLAMINE DERIVATIVES AS MELATONERGICS

This application is a continuation-in-part of U.S. Ser. No. 08/486,633 filed Jun. 7, 1995.

BACKGROUND OF THE INVENTION

The invention pertains to novel N-acyl 2-arylcyclopropylmethylamine derivatives having drug and bio-affecting properties, to their preparation, to pharmaceutical formulations containing them and to methods of using them. These compounds possess melatonergic properties that should make them useful in treating certain medical disorders.

Melatonin (i; N-acetyl-5-methoxytryptamine) is a hormone which is synthesized and secreted primarily by the pineal gland. In mammals, melatonin levels show a cyclical, circadian pattern, with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

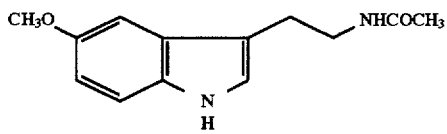

Recent evidence demonstrates that melatonin exerts its biological effects through specific receptors. Use of the biologically active, radiolabelled agonist $[^{125}I]$-2-iodomelatonin has led to the identification of high affinity melatonin receptors in the central nervous systems (CNS) of a variety of species. The sequence of one such high affinity melatonin receptor, cloned from frog melanocytes, has been reported. In mammalian brain, autoradiographic studies have localized the distribution of melatonin receptors to a few specific structures.

Although there are significant differences in melatonin receptor distribution even between closely related species, in general the highest binding site density occurs in discrete nuclei of the hypothalamus. In humans, specific $[^{125}I]$-2-iodomelatonin binding within the hypothalamus is completely localized to the suprachiasmatic nucleus, strongly suggesting that melatonin receptors are located within the human biological clock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487.

Melatonin binding sites have been found in diverse tissues of the body—i.e., in the retina, superchiasmatic nucleus, spleen, etc. This means that melatonin exerts multiple physiological effects and is not highly selective. The potential for side effects with melatonin use is large. Melatonin agonists should be more selective than melatonin and have fewer side effects. Suitable melatonin agonists could overcome melatonin's drawbacks, resulting in products having more predictable and, possibly, sustained activity.

Melatonin agonists should be particularly useful for the treatment of chronobiological disorders. They would also be useful for the further study of melatonin receptor interactions as well as in the treatment of conditions affected by melatonin activity, such as depression, work-shift syndrome, sleep disorders, glaucoma, reproduction, cancer, immune disorders, neuroendorine disorders, and a variety of sleep disorders.

Aside from simple indole derivatives of melatonin itself, various amide structures have been prepared and their use as melatonin ligands disclosed. In general these amide structures can be represented as:

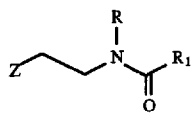

wherein Z is an aryl or heteroaryl system attached by a two carbon chain to the amide group. Some specific examples follow.

Yous, et al. in European Patent Application EPA 527 687A disclose, as melatonin ligands, ethylamines having cyclic substituents, 1,

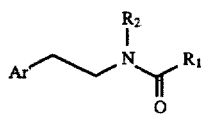

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Langlois, et al., in Australian Patent Application AU-A48729/93 disclose arylalkyl(thio)amides 2 as melatonergic ligands.

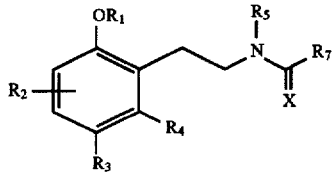

wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl; $R_5$ is hydrogen or lower alkyl; X is sulfur or oxygen and $R_7$ is, inter alia, lower alkyl or alkenyl.

However, these references do not teach or suggest the novel melatonergic aryl cyclopropylmethylamine derivatives of the present invention.

A number of compounds containing structural elements common to the compounds of the present invention have been disclosed, although melatonergic properties have not been claimed for any the compounds within these disclosures.

Matsuda, et al., in international patent application WO 95/22521 disclose 1-phenyl-2-(1-aminoalkyl)-N,N-diethylcyclopropanecarboxamides 3 as N-methyl-D-aspartate (NMDA) receptor antagonists, wherein $R_1$ represents, inter alia, a $C_1$–$C_5$ linear saturated aliphatic, a $C_1$–$C_5$ linear unsaturated aliphatic, a branched aliphatic, or a phenyl group which may be substituted with one to three substituents selected independently from the group consisting of halogen, $C_1$–$C_4$ alkyl, nitro, amino, hydroxy, and $C_1$–$C_4$ alkoxy.

The 1,2-diarylcyclopropane derivatives of type 4 are disclosed in NE 6701256 as having CNS stimulant properties.

$Ar_1$ and $Ar_2$ are independently and optionally substituted phenyl; $R_1$ is inter alia hydrogen, lower alkyl or acyl; $R_2$ is inter alia alkyl, cycloalkyl or aralkyl.

SUMMARY OF THE INVENTION

The present invention is concerned with compounds of Formula I, which possess melatonergic properties and thus have utility in the treatment of conditions affected by melatonin activity:

wherein:

X is halogen, hydrogen, $C_{1-4}$ alkyl or $OR_5$, wherein $R_5$ is hydrogen, $C_{1-4}$ perfluoroalkyl, $C_{1-4}$ fluoroalkyl, $C_{1-4}$perdeuteroalkyl, $C_{1-20}$ alkyl, $C_{4-20}$ alkcycloalkyl, $C_{2-20}$ carbonitriloalkyl, $C_{3-22}$ carboalkoxyalkyl, $C_{3-20}$ alkenyl, $C_{3-20}$ alkynyl, $C_{9-20}$ aralkyl, $C_{9-20}$ aralkenyl, $C_{9-20}$ aralkynyl, $C_{2-20}$ hydroxyalkyl, $C_{8-20}$ aryloxyalkyl, $C_{7-20}$ pyridylalkyl, or $C_{6-20}$ pyrrylalkyl;

Y is hydrogen or halogen;

Z is hydrogen, halogen, cyano, aryl, $C_{7-20}$ aralkyl, $C_{8-20}$ arylkynyl, or $C_{2-20}$ alkamido;

R, in both cases, is hydrogen, halogen, or $C_{1-4}$ alkyl;

G is a divalent methylene, ethylene, or $C_{1-4}$ alkmethylene moiety;

$R_1$ is hydrogen, $C_{1-4}$ alkyl or benzyl; and $R_2$ is $C_{1-6}$ alkyl, $C_{2-6}$ alkenyl, $C_{3-6}$ cycloalkyl, $C_{2-4}$ alkoxyalkyl, $C_{1-4}$ trifluoromethylalkyl, $C_{2-8}$ alkylthioalkyl or $NR_3R_4$, wherein $R_3$ and $R_4$ are independently selected from hydrogen and $C_{1-4}$ alkyl, but $R_3$ and $R_4$ cannot both be hydrogen.

DETAILED DESCRIPTION OF THE INVENTION

This invention deals with compounds of Formula I, their preparation and their use in methods and compositions for treating certain conditions.

Formula I is:

wherein:

X is halogen, hydrogen, $C_{1-4}$ alkyl or $OR_5$, wherein $R_5$ is hydrogen, $C_{1-4}$ perfluoroalkyl, $C_{1-4}$ fluoroalkyl, $C_{1-4}$ perdeuteroalkyl, $C_{1-20}$ alkyl, $C_{4-20}$ alkcycloalkyl, $C_{2-20}$ carbonitriloalkyl, $C_{3-22}$ carboalkoxyalkyl, $C_{3-20}$ alkenyl, $C_{3-20}$ alkynyl, $C_{9-20}$ aralkyl, $C_{9-20}$ aralkenyl, $C_{9-20}$ aralkynyl, $C_{2-20}$ hydroxyalkyl, $C_{8-20}$ aryloxyalkyl, $C_{7-20}$ pyridylalkyl, or $C_{6-20}$ pyrrylalkyl;

Y is hydrogen or halogen;

Z is hydrogen, halogen, cyano, aryl, $C_{7-20}$ aralkyl, $C_{8-20}$ arylkynyl, or $C_{2-20}$ alkamido;

R, in both cases, is hydrogen, halogen, or $C_{1-4}$ alkyl;

G is a divalent methylene, ethylene, or $C_{1-4}$ alkmethylene moiety;

$R_1$ is hydrogen, $C_{1-4}$ alkyl or benzyl; and $R_2$ is $C_{1-6}$ alkyl, $C_{2-6}$ alkenyl, $C_{3-6}$ cycloalkyl, $C_{2-4}$ alkoxyalkyl, $C_{1-4}$ trifluoromethylalkyl, $C_{2-8}$ alkylthioalkyl or $NR_3R_4$, wherein $R_3$ and $R_4$ are independently selected from hydrogen and $C_{1-4}$ alkyl, but $R_3$ and $R_4$ cannot both be hydrogen.

It is to be understood that, as used herein, "halogen" denotes fluorine, chlorine, bromine and iodine; the term "alkyl" refers to straight and branched chain saturated hydrocarbon radicals; "fluoroalkyl" refers to straight and branched chain monofluorosubstituted saturated hydrocarbon radicals; "alkenyl" refers to straight and branched hydrocarbon radicals containing a carbon-carbon double bond; "cycloalkyl" refers to saturated cyclic hydrocarbon radicals; "alkoxy" denotes an alkyl radical connected to a molecule via an oxygen atom; "alkylthioalkyl" refers to an alkyl radical linked to another via a sulfur atom; "aryloxyalkyl" refers to an alkyl radical linked to an optionally substituted phenyl group via an oxygen atom; "alkcycloalkyl" refers to an alkyl radical linked to a saturated cyclic hydrocarbon radical; "carbonitriloalkyl" refers to an alkyl radical linked to a nitrilo radical via a carbon atom; "carboalkoxyalkyl" refers to an alkyl radical linked directly to a carboalkoxy radical; "hydroxyalkyl" refers to an alkyl radical linked to a hydrogen atom via an oxygen atom; "pyridylalkyl" refers to a pyridyl radical linked directly to the terminal carbon of an alkyl radical; "pyrrylalkyl" refers to a pyrryl radical linked directly to the terminal carbon of an alkyl radical; "trifluoromethylalkyl" refers to a trifluoro-substituted methyl group linked directly to an alkyl radical; "perfluoralkyl" refers to straight and branched chain saturated fluorocarbon radicals; "perdeuteroalkyl" refers to straight and branched chain saturated deuterocarbon radicals; "cyano" refers to a radical containing a carbon-nitrogen triple bond; "alkynyl" refers to straight and branched hydrocarbon radicals containing a carbon-carbon triple bond; "aralkyl", "aralkenyl", and "aralkynyl" (or "arylalkyl", "arylalkenyl" and "arylalkynyl", respectively) refer to radicals in which an optionally substituted phenyl group is appended to the terminal carbon of an alkyl, alkenyl or alkynyl radical respectively; "alkamido" (or "alkylamido") refers to —NC(O)-alkyl groups containing the stated number of carbon atoms; "alkmethylene" (or "alkylmethylene") refers to an alkyl radical attached directly to a methene radical. "Benzyl"

or "Bn" refers to the phenylmethyl group, —CH$_2$-phenyl. Phenyl groups, when present, bear substituents selected from hydrogen, halogen, trifluoromethyl and C$_{1-4}$ alkoxy moieties.

Numbers recited in subscripts immediately following "C" denote the number of carbon atoms in the moiety.

Based upon biological tests, the following Formula I compounds are preferred. All have binding affinities for the human melatonin receptor with IC$_{50}$ values of 600 nM or less.

Preferred compounds of formula I are those wherein R$_1$ is hydrogen, R$_2$ is C$_{1-4}$ alkyl, Y and Z are independently hydrogen or halogen, and X is OR$_5$, wherein R$_5$ is C$_{1-20}$ alkyl, C$_{3-20}$ alkenyl, C$_{3-20}$ alkynyl, and C$_{9-20}$ aralkyl, aralkenyl or aralkynyl. It is preferred that R$_2$ be devoid of O, N and S atoms. It is highly preferred that R$_2$ be C$_{1-4}$ alkyl.

Preferred compounds of the present invention include those in the following list:

(trans)-N-[[2-(3-Methoxyphenyl)cyclopropyl]methyl] butanamide;

(trans)-N-[[2-(3-Methoxyphenyl)cyclopropyl]methyl]-2-methoxyacetamide;

(+)-(trans)-N-[[2-(3-Methoxyphenyl)cyclopropyl]-methyl] butanamide;

(−)-(trans)-N-[[2-(3-Methoxyphenyl)cyclopropyl]methyl] butanamide;

(trans)-N-[[2-(3-Methoxyphenyl)cyclopropyl]methyl] propanamide;

(trans)-N-[[2-(4Chloro-3-methoxyphenyl)cyclopropyl] methyl] butanamide;

(−)-(trans)-N-[[2-(3-Methoxyphenyl)cyclopropyl]methyl]-2-methylpropanamide;

(trans)-N-[[2-[3-(6-Phenylhexyl)oxy]phenyl]cyclopropyl] methyl] butanamide;

(trans)-N-[[2-(2-Bromo-5-methoxyphenyl)cyclopropyl] methyl]butanamide;

(trans)-N-[[2-(3-Methoxyphenyl)cyclopropyl]methyl] acetamide;

(−)-(trans)-N-[[2-(2,4-Dibromo-5-methoxyphenyl)-cyclopropyl]methyl] butanamide;

(trans)-N-[[2-(2-Iodo-5-methoxyphenyl)cyclopropyl] methyl] butanamide;

(−)-(trans)-N-[[2-(2-Iodo-5-methoxyphenyl)cyclopropyl] methyl] butanamide;

(trans)-N-[[2-[3-(Heptyloxy)phenyl]cyclopropyl]methyl] butanamide;

(trans)-N-[[2-[3-(2-Propenyloxy)phenyl]cyclopropyl] methyl] butanamide;

(trans)-N-[[2-[3-[(7-Phenylheptyl)oxy]phenyl]cyclopropyl] methyl] butanamide;

(trans)-N-[[2-(3-[(Ethoxyphenyl)cyclopropyl]methyl] butanamide;

(trans)-N-[[2-[(3-Octyloxy)phenyl]cyclopropyl]methyl] butanamide;

(trans)-N-[[2-[3-(Nonyloxy)phenyl]cyclopropyl]methyl] butanamide;

(trans)-N-[[2-[(3-Decyloxy)phenyl] cyclopropyl]methyl] butanamide;

(trans)-N-[[2-[(3-Undecyloxy)phenyl]cyclopropyl]methyl] butanamide;

(trans)-N-[[2-[(3-Dodecyloxy)phenyl]cyclopropyl]methyl] butanamide;

(trans)-N-[[2-[3-[(2-Phenylethyl)oxy]phenyl]cyclopropyl] methyl] butanamide;

(trans)-N-[[2-[3-[3-(3-Methoxyphenyl)propoxy]phenyl] cyclopropyl]methyl] butanamide;

(−)-(trans)-N-[[2-(5-Methoxy-2-(phenylethynyl)phenyl) cycloprop-1-yl]methyl] butanamide;

(trans)-N-[[3-(3-Methoxyphenyl)-2,2-difluoro-1-cycloprop-1-yl]methyl] butanamide;

(−)-(trans)-N-[[2-(3-Methoxyphenyl)cycloprop-1-yl] methyl]cyclopropane carboxamide;

(−)-(trans)-N-[[2-[3-[3-(3-Methoxyphenyl)propoxy]phenyl] cycloprop-1-yl)methyl] butanamide;

(−)-(trans)-N-[[2-(3-Methoxyphenyl)cycloprop-1-yl] methyl]-N'-methyl urea;

(−)-(trans)-N-[[2-(3-Methoxyphenyl)cycloprop-1-yl] methyl] propanamide;

(−)-(trans)-N-[[2-(3-Methoxyphenyl)cycloprop-1-yl] methyl] acetamide;

(−)-(trans)-3,3,3-Trifluoro-N-[[2-(3-methoxyphenyl) cycloprop-1-yl]methyl] propanamide;

(trans)-N-[[2-[3-[(3-,7,11-Trimethyldodeca-2,6,10-trien-1-yl)oxy]phenyl]cycloprop-1-yl]methyl] butanamide;

(trans)-N-[[2-[3-[(4-Phenylbut-1-yl)oxy]phenyl]cycloprop-1-yl]methyl] butanamide;

(trans)-N-[[2-[3-[(5-Phenylpent-1-yl)oxy]phenyl] cycloprop-1-yl]methyl] butanamide;

(trans)-N-[2-[(3-Trideuteromethoxyphenyl)cycloprop-1-yl] methyl] butanamide;

(trans)-N-[[2-[3-[(3-Cyclohexylprop-1-yl)oxy]phenyl] cycloprop-1-yl]methyl] butanamide;

(trans)-N-[[2-[3-[(3-Cyclopentylprop-1-yl)oxy]phenyl] cycloprop-1-yl]methyl] butanamide;

(trans)-N-[[2-[3-[2-[3-(Trifluoromethyl)phenyl]ethoxy] phenyl]cycloprop-1-yl]methyl] butanamide;

(trans)-N-[[2-[3-[(2-(3-Methoxyphenyl)cycloprop-1-yl] methoxy]phenyl]cycloprop-1-yl]methyl] butanamide;

(trans)-N-[[2-(4-Chloro-3-methoxyphenyl)cyclopropyl] methyl] butanamide;

(trans)-N-[[2-(3-Methoxyphenyl)cyclopropyl]methyl]-2-methylthioacetamide;

(trans)-N-[[2-[3-[3-(3-Methoxyphenyl)propoxy]phenyl] cyclopropyl]methyl] butanamide;

(−)-(trans)-N-[[2-(4-Iodo-3-methoxyphenyl)cycloprop-1-yl]methyl] butanamide;

(−)-(trans)-N-[[2-(5-Methoxy-2-(phenylethyl)phenyl) cycloprop-1-yl]methyl] butanamide;

(−)-(trans)-N-[[2-(4-Methoxy-[1,1'-biphenyl]-2yl-cycloprop-1-yl]methyl] butanamide;

(−)-(trans)-N-[[2-[4-Methoxy-4'-(trifluoromethyl) [1,1'-biphenyl]-2yl]cycloprop-1-yl]methyl] butanamide;

(trans)-N-[[2-(3-Bromophenyl)cycloprop-1-yl]methyl] butanamide;

(trans)-N-[[2-(3-Bromophenyl)cycloprop-1-yl]methyl] acetamide;

(trans)-N-[[2-(3-Bromophenyl)cycloprop-1-yl]methyl] propanamide;

(−)-(trans)-N-[[2-[2-Iodo-5-[3-(3-methoxyphenyl)propoxy] phenyl]cycloprop-1-yl)methyl] butanamide;

(trans)-N-[[2-[3[(3-Phenylprop-1-yl)oxy] phenyl] cycloprop-1-yl]methyl] butanamide;

(trans)-N-[[2-[3[(3-Phenoxyprop-1-yl)oxy] phenyl] cycloprop-1-yl]methyl] butanamide;

(trans)-N-[[2-[3[(3-Dimethylocta-2,6-dien-1-yl)oxy] phenyl] cycloprop-1-yl]methyl] butanamide;

(trans)-N-[[2-[3-(5-Methylhexyloxy)phenyl] cycloprop-1-yl]methyl] butanamide;

(trans)-N-[[2-[3-(4-Methyl-3-penten-1-yloxy)phenyl] cycloprop-1-yl]methyl] butanamide;

(trans)-N-[[2-[3-[(3-Cyclohexylbut-1-yl)oxy]phenyl] cycloprop-1-yl]methyl] butanamide;

(trans)-N-[[2-[3-[2-[2-(Trifluoromethyl)phenyl]ethoxy] phenyl]cycloprop-1-yl]methyl] butanamide;

(trans)-N-[[2-[3-[2-(3-Fluorophenyl) ethoxy]phenyl] cycloprop-1-yl]methyl] butanamide;
(trans)-N-[[2-[3-[3-(4-Methoxyphenyl) propoxy]phenyl] cycloprop-1-yl]methyl] butanamide;
(trans)-N-[[2-[3-[2-(2-Fluorophenyl) ethoxy] phenyl] cycloprop-1-yl]methyl] butanamide;
(trans)-N-[[2-[3-[2-(2-Methoxyphenyl) ethoxy] phenyl] cycloprop-1-yl]methyl] butanamide;
(–)-(trans)-N-[[2-(3-Fluorophenyl)cyclopropyl]methyl] butanamide;
(–)-(trans)-N-[[2-(3-Fluorophenyl)cycloprop-1-yl]methyl]-2-methylpropanamide;
(–)-(trans)-N-[[2-(2-Bromo-5-fluorophenyl)cycloprop-1-yl]methyl] butanamide;
(–)-(trans)-N-[[2-(4-Bromo-3-fluorophenyl)cycloprop-1-yl]methyl] butanamide;
(–)-(trans)-N-[[2-(5-Fluoro-2-iodophenyl)cycloprop-1-yl]methyl] butanamide;
(–)-(trans)-N-[[2-(3-Fluoro-4-iodophenyl)cycloprop-1-yl]methyl] butanamide;
(trans)-N-[[3-(3-Methoxyphenyl)-2,2-difluoro-1-cycloprop-1-yl]methyl] butanamide;
(trans)-N-[[3-(3-Methoxyphenyl)-2,2-difluoro--cycloprop-1-yl]methyl]-2-methylpropanamide;
(trans)-N-[[2-(3-Bromophenyl)cycloprop-1-yl]methyl] butanamide;
(trans)-N-[[2-(3-Bromophenyl)cycloprop-1-yl]methyl] acetamide;
(trans)-N-[[2-(3-Methylphenyl)cycloprop-1-yl]methyl] butanamide;
(trans)-N-[[2-(3-Bromophenyl)cycloprop-1-yl]methyl] propanamide;
(trans)-N-[[2-(3-Methylphenyl)cycloprop-1-yl]methyl]-2-methylpropanamide;
(trans)-N-[[2-(3-Methylphenyl)cycloprop-1-yl]methyl] acetamide;
(trans)-N-[[2-(3-Chlorophenyl)cycloprop-1-yl]methyl] butanamide;
(trans)-N-[[2-(3-Chlorophenyl)cycloprop-1-yl]methyl] propanamide;
(trans)-N-[[2-(3-Chlorophenyl)cycloprop-1-yl]methyl] acetamide;
(trans)-N-[[2-(3-Chlorophenyl)cycloprop-1-yl]methyl] cyclopropane carboxamide;
(trans)-N-[[2-(2,5-Difluorophenyl)cycloprop-1-yl]methyl] acetamide;
(trans)-N-[[2-(2,5-Difluorophenyl)cycloprop-1-yl]methyl] propanamide;
(trans)-N-[[2-(2,5-Difluorophenyl)cycloprop-1-yl]methyl] butanamide;
(trans)-N-[[2-(2,5-Difluorophenyl)cycloprop-1-yl]methyl] cyclopropane carboxamide;
(trans)-N-[[2-[3-(Pentafluoroethyl)phenyl]cycloprop-1-yl]methyl] butanamide;
(–)-(trans)-N-[(2-Phenylcycloprop-1-yl)methyl] butanamide;
(trans)-N-[(2-Phenylcycloprop-1-yl) methyl] acetamide;
(trans)-N-[(2-Phenylcycloprop-1-yl) methyl] butanamide;
(trans)-N-[2-[(3-Ethylphenyl) cycloprop-1-yl]methyl] acetamide;
(trans)-N-[2-[(3-Ethylphenyl) cycloprop-1-yl]methyl] propanamide;
(trans)-N-[2-[(3-Ethylphenyl) cycloprop-1-yl]methyl] butanamide;
(trans)-N-[2-[(3-Ethylphenyl) cycloprop-1-yl]methyl] cyclopropanecarboxamide;
(trans)-N-[[2-[3-(Trifluoromethyl)phenyl]cycloprop-1-yl]methyl] butanamide;
(trans)-N-[[2-[3-(Trifluoromethyl)phenyl]cycloprop-1-yl]methyl]-2-methylpropanamide;
(–)-(trans)-N-[[2-(2-Bromo-5-fluorophenyl)cycloprop-1-yl]methyl] butanamide;
(trans)-N-[[2-(3-Methylphenyl)cycloprop-1-yl]methyl] butanamide; and
(trans)-N-[2-[(3-Ethylphenyl)cycloprop-1-yl]methyl] butanamide.

The compounds of Formula I can be prepared as depicted in the following schemes (Processes 1–8). The groups R, $R_1$, $R_2$, $R_3$, $R_4$ X, Y, Z, G and $R_5$ are as defined herein above.

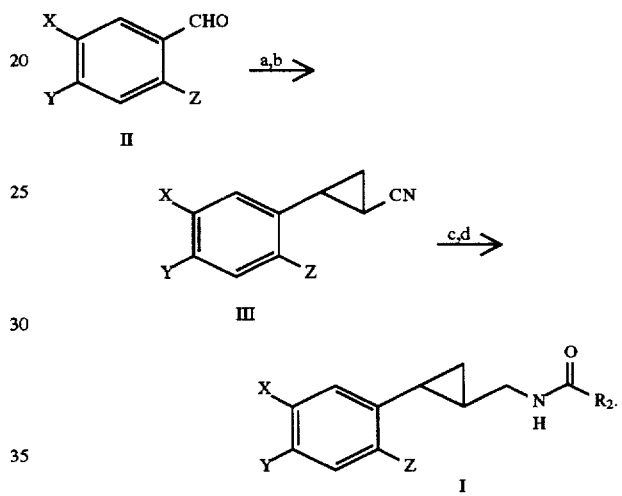

Process I

<sup>a</sup>diethyl cyanomethylphosphonate, NaH, THF.
<sup>b</sup>trimethylsulfoxonium iodide, NaH, DMSO.
<sup>c</sup>H$_2$, PtO$_2$, CHCl$_3$/EtOH.
<sup>d</sup>acylation: R$_2$COCl, base In the resultant Formula I compounds, $R_1$ and R are H. G is methylene, and the other substitutents are as defined above.

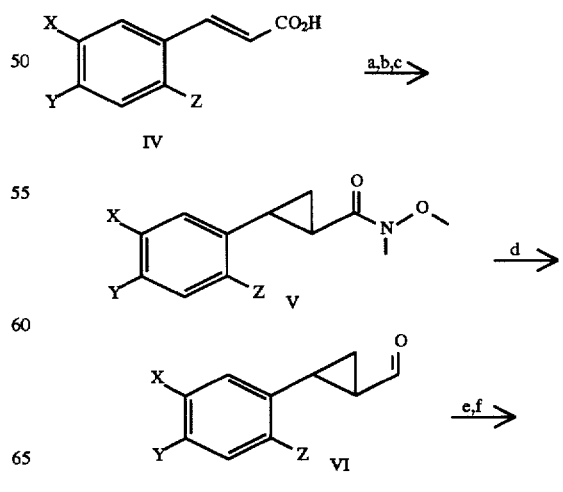

Process 2

-continued
Process 2

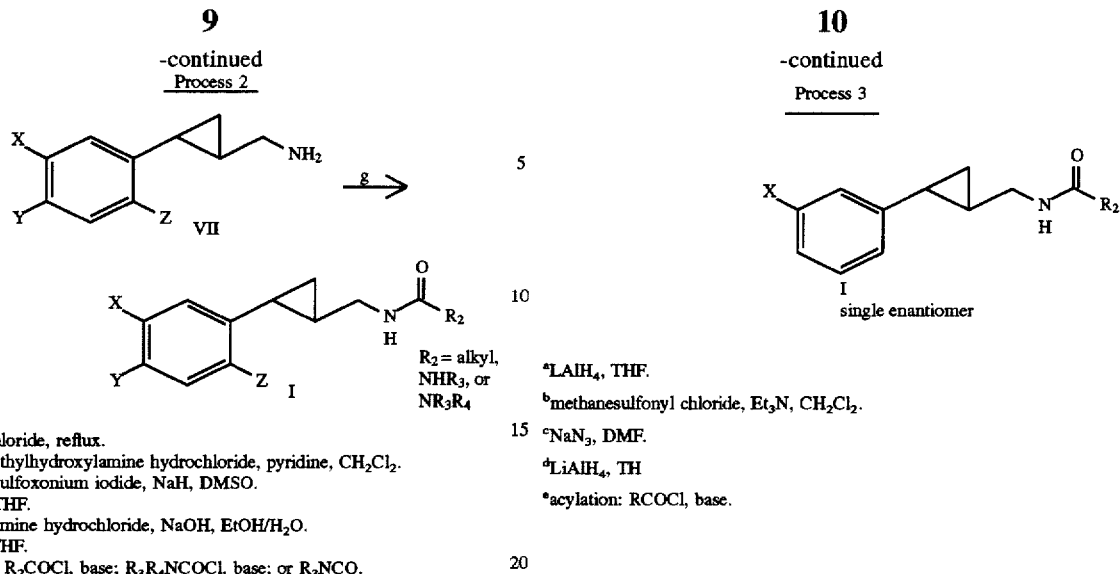

*thionyl chloride, reflux.
ᵇN,O-dimethylhydroxylamine hydrochloride, pyridine, CH₂Cl₂.
ᶜtrimethylsulfoxonium iodide, NaH, DMSO.
ᵈLiAlH₄, THF.
ᵉhydroxylamine hydrochloride, NaOH, EtOH/H₂O.
ᶠLiAlH₄, THF.
ᵍacylation: R₂COCl, base; R₃R₄NCOCl, base; or R₃NCO.

Using Process 2, the R₂ group in the final formula I compound is alkyl, NHR₃, or NR₃R₄ (as defined above). G is methylene; R₁ and R are H.

-continued
Process 3

(structure I, single enantiomer)

ᵃLAlH₄, THF.
ᵇmethanesulfonyl chloride, Et₃N, CH₂Cl₂.
ᶜNaN₃, DMF.
ᵈLiAlH₄, TH
ᵉacylation: RCOCl, base.

In Formula I compounds made using Process 3, R₁, R, Y and Z are all H, and G is methylene.

Processes 4, 5

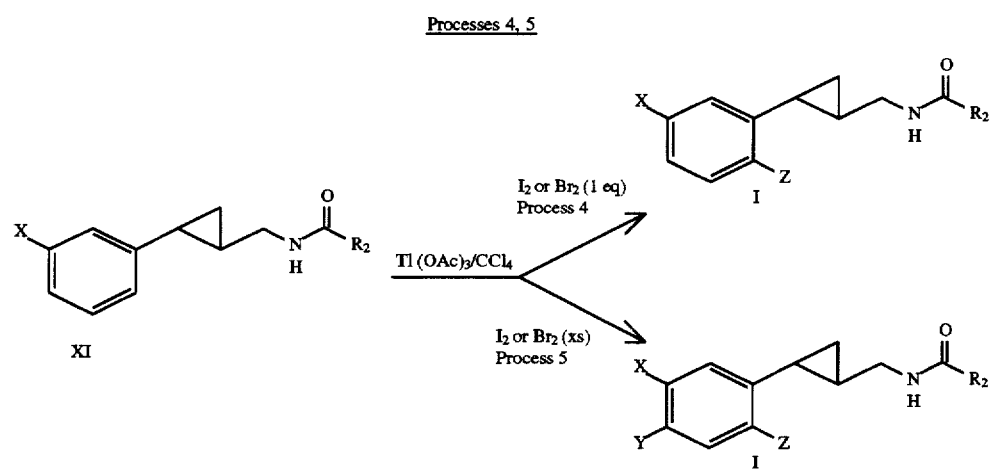

When using Process 4, the Formula I compounds made are those in which G is methylene; Y, R₁, and R are H, and Z is Br or I. Formula I compounds produced via Process 5 are those wherein Y and Z are both Br or I, G is methylene, and R₁ and R are H.

Process 3

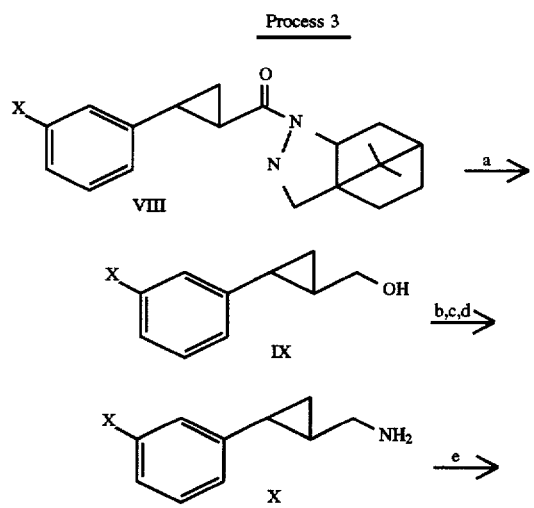

Process 6

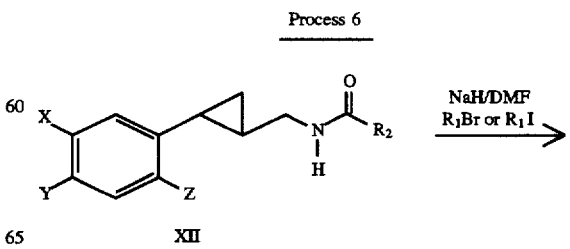

-continued

Process 6

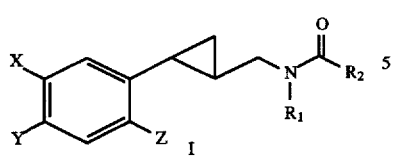

Via Process 6, the Formula I compounds made are those in which $R_1$ is $C_{1-4}$ alkyl or benzyl, G is methylene, R is H, and $R_2$, X, Y, Z are as defined above.

Processes 7, 8

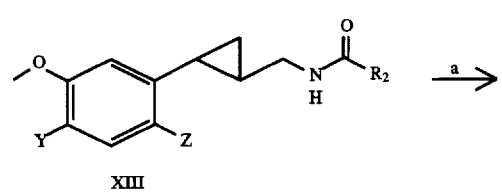

XIII

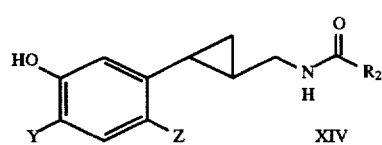

XIV

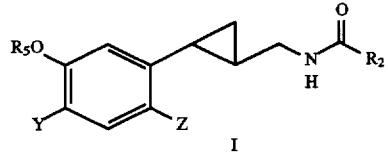

I

ªBBr$_3$, CH$_2$Cl$_2$.
ᵇBase, R$_5$I or R$_5$Br. (Process 7)

In Processes 7 and 8, the final Formula I compounds are those in which G is methylene, X is OR$_5$, $R_1$ and R are H, and Y, Z, $R_2$ and $R_5$ have the definitions given above.

Process 9

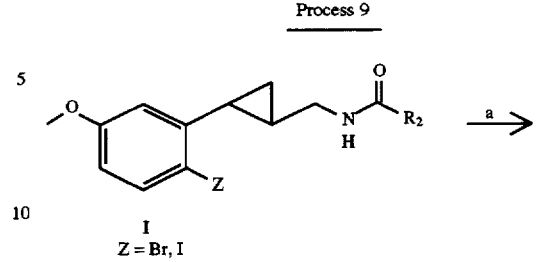

I
Z = Br, I

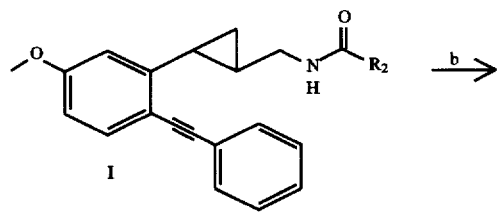

I

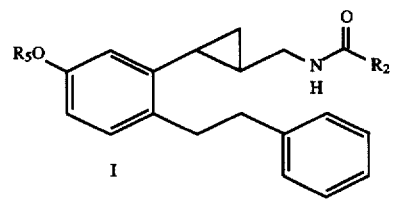

I

ªPhCCH, Pd(Ph$_3$P)$_4$, Et$_3$N, reflux.
ᵇH$_2$, Pd/C, EtOH.

Via Process 9, the formula I compounds wherein X is OCH$_3$, G is methylene, Z is phenylalkyne or hydrocinnamyl, and $R_1$, R and Y are hydrogen are produced.

Processes 10, 11

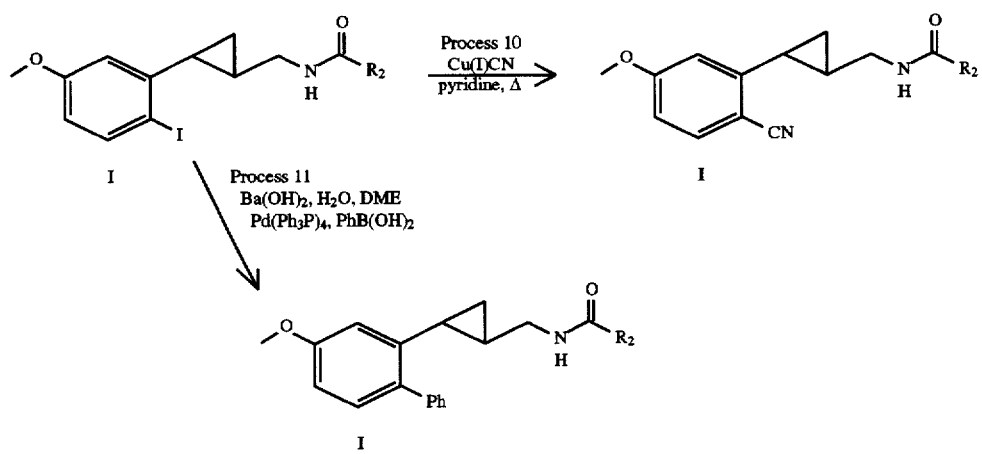

Via Process 10, the formula I compounds wherein X is OCH$_3$, G is methylene, Z is cyano, and $R_1$, R and Y are hydrogen are produced. Via Process 11, the formula I compounds wherein X is OCH$_3$, G is methylene, Z is phenyl, and $R_1$, R and Y are hydrogen are produced.

Process 12

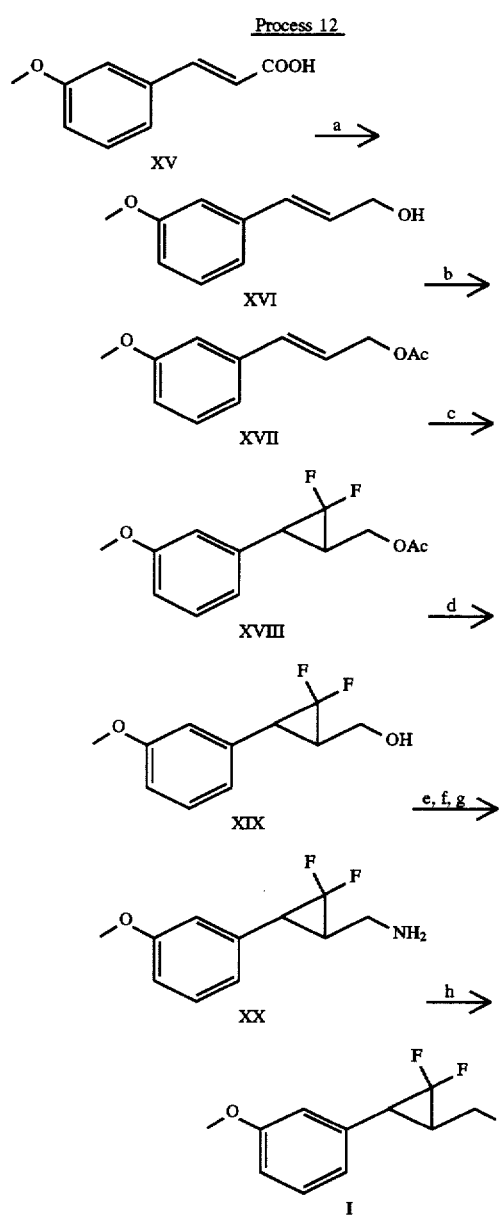

$^a$1) NaBH$_4$, THF 2) I$_2$, THF 3) H$^+$. $^b$Ac$_2$O, pyridine. $^c$FCl$_2$CCOONa, diglyme, reflux. $^d$KOH, methanol, THF. $^e$CH$_3$SO$_2$Cl, Et$_3$N, CH$_2$Cl$_2$. $^f$NaN$_3$, DMF. $^g$LiAlH$_4$, Et$_2$O. $^h$R$_2$COCl, Et$_3$N, CH$_2$Cl$_2$.

Via Process 12, the formula I compounds wherein X is OCH$_3$, R is fluorine, G is methylene, and Z, $R_1$, and Y are hydrogen are produced.

Process 13

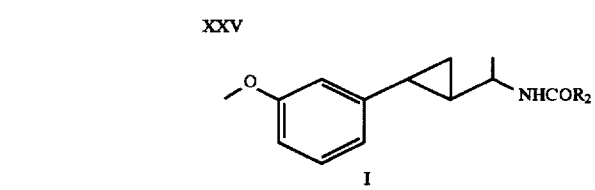

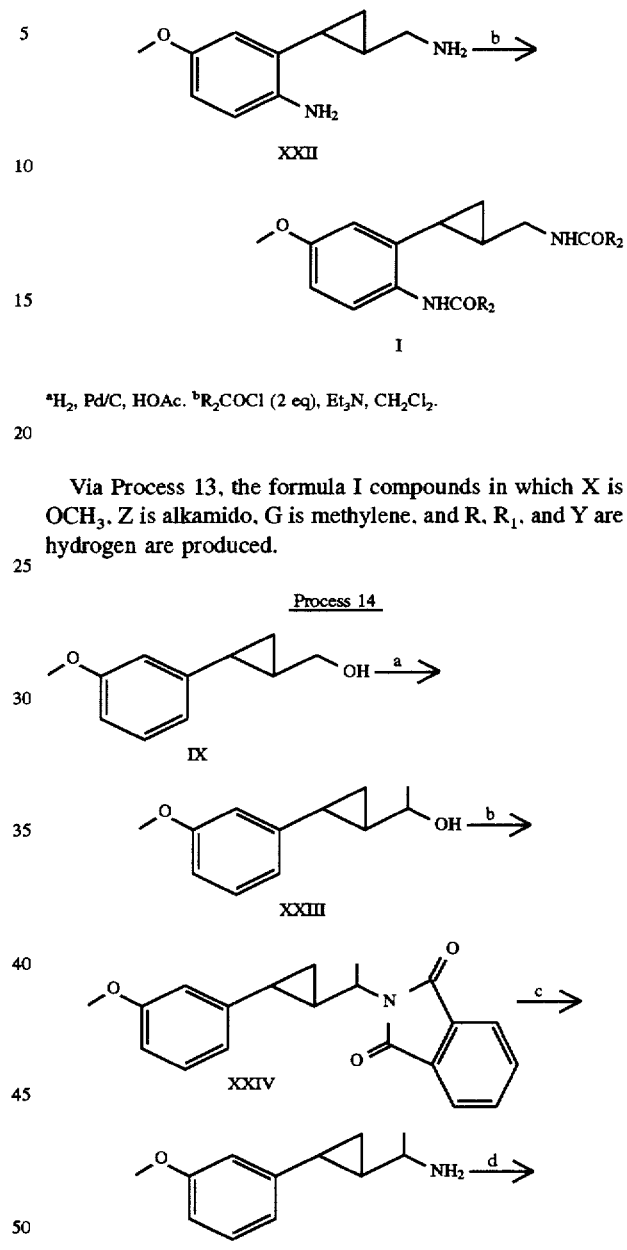

$^a$H$_2$, Pd/C, HOAc. $^b$R$_2$COCl (2 eq), Et$_3$N, CH$_2$Cl$_2$.

Via Process 13, the formula I compounds in which X is OCH$_3$, Z is alkamido, G is methylene, and R, $R_1$, and Y are hydrogen are produced.

Process 14

$^a$1) oxalyl chloride, DMSO, CH$_2$Cl$_2$ 2) MeMgBr, THF 3) separate. $^b$Ph$_3$P, EtO$_2$CNNCO$_2$Et phthalimide, THF. $^c$hydrazine, EtOH $^d$R$_2$COCl, Et$_3$N, CH$_2$Cl$_2$.

Via Process 14, the formula I compounds wherein X is OCH$_3$, G is alkmethylene, and R, $R_1$, Z, and Y are hydrogen are produced.

Process 15

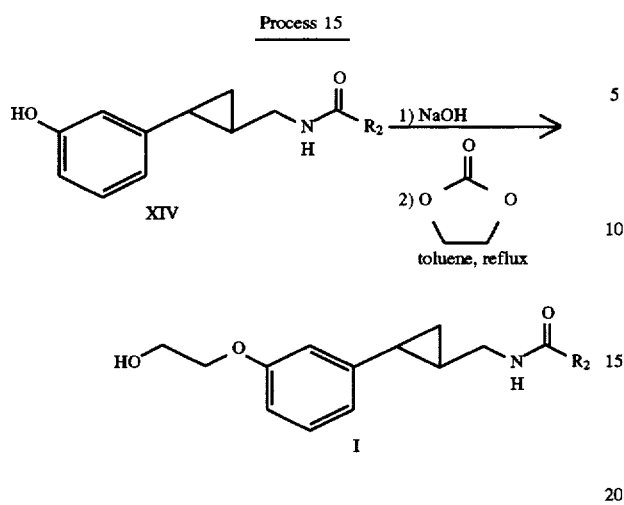

Via Process 15, the formula I compounds wherein X is 2-hydroxyethyl, G is methylene, and R, R₁, Z, and Y are hydrogen are produced.

Process 16

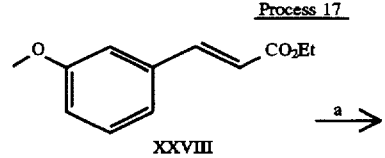

$^a$1) CH₃SO₂Cl, Et₃N 2) NaCN, DMF, Δ. $^b$LiAlH₄, THF. $^c$R₂COCl, Et₃N, CH₂Cl₂.

Via Process 16, the formula I compounds wherein X is OCH₃, G is ethylene, and R, R₁, Z, and Y are hydrogen are produced.

Process 17

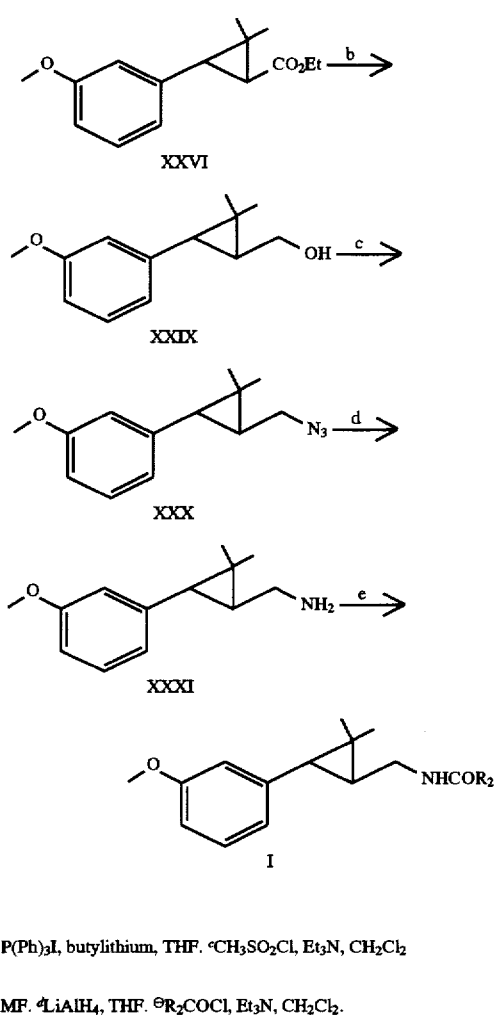

$^a$ P(Ph)₃I, butyllithium, THF. $^c$CH₃SO₂Cl, Et₃N, CH₂Cl₂

2) NaN₃, DMF. $^d$LiAlH₄, THF. $^e$R₂COCl, Et₃N, CH₂Cl₂.

Via Process 17, the formula I compounds wherein X is OCH₃, G is methylene, R is methyl, and R₁, Z, and Y are hydrogen are produced.

Unless stated otherwise, all substituents on the Formula I compounds produced via Processes 1–17 may have any of the definitions recited in the first discussion of Formula I herein.

The preparation of Compounds of Formula I involves the following steps described for each of Processes 1–17:

Process 1 (Reactions a–d)

(i) Treatment of commercially available aldehydes of Formula II with sodium hydride and cyanomethylphosphonate, followed by cyclopropanation with dimethyloxosulphonium methylide gave intermediate cyclopropane nitrites of Formula III.

(ii) Catalytic reduction of nitrites III by hydrogen in the presence of platinum oxide, followed by acylation of the resultant amine with an appropriate acyl chloride, gave compounds of Formula I, wherein R₁ is hydrogen.

Process 2 (Reactions a–g)

(i) Treatment of commercially available cinnamic acids of Formula IV with refluxing thionyl chloride, followed by acylation with N,O-dimethylhydroxylamine hydrochloride in the presence of pyridine gave unsaturated N-methyl,N-methoxy amides which were cyclopropanated with dimethyloxophosphonium methylide to give intermediates of Formula V.

(ii) Reduction of amides V with lithium aluminum hydride gave aldehydes of formula VI.

(iii) Aldehydes VI were converted to oximes with hydroxylamine hydrochloride and sodium hydroxide, and reduced with lithium aluminum hydride to give amines of Formula VII.

(iv) Compounds of formula VII were acylated with appropriate acylating agents, such as acyl chlorides, carbamoyl chlorides, or isocyanates to give compounds of Formula I, wherein $R_1$ is hydrogen, and $R_2$ is alkyl, $NR_3R_4$, or $NHR_3$ as defined previously.

Process 3 (Reactions a–e)

(i) Reduction of the known homochiral sultams VIII with lithium aluminum hydride produced alcohols IX as single enantiomers.

(ii) Conversion of alcohols IX to the corresponding methanesulfonate esters with methanesulfonyl chloride and triethylamine, followed by azide formation with sodium azide in dimethylformamide, and lithium aluminum hydride reduction gave enantiopure amines of Formula X.

(iii) Amines X were acylated with appropriate acyl chlorides to give compounds of Formula I wherein $R_1$ is hydrogen and Y and Z are hydrogen.

Process 4

Amides XI, produced by Processes I, II or III, were treated with thallium (III) acetate and 1 equivalent of bromine or iodine to give compounds of Formula I wherein Y is hydrogen, Z is bromine or iodine, and $R_1$ is hydrogen.

Process 5

Amides XI, produced by Processes I, II or III, were treated with thallium (III) acetate and 2 or more equivalents of bromine or iodine to give compounds of Formula I wherein Y is equal to Z is equal to bromine or iodine, and $R_1$ is hydrogen.

Process 6

Amides XII, produced by Processes I, II or III, were treated with sodium hydride and an appropriate alkyl or benzylhalide to give compounds of Formula I wherein $R_1$ is $C_{1-4}$ alkyl or benzyl.

Process 7

(i) Amides XIII, produced by Processes I, II or III, were treated with boron tribromide to produce compounds of Formula XIV.

(ii) Amides XIV were treated with base and the resultant alkoxides were alkylated with appropriate alkyl iodides or alkyl bromides to produce compounds of Formula I wherein X is $OR_5$ and $R_1$ is hydrogen.

Process 8

(i) Amides XIII, produced by Processes I, II or III, were treated with boron tribromide to produce compounds of Formula XIV.

(ii) Amides XIV were added to a prepared solution of an appropriate alcohol, triphenylphosphine, and diethyl azodicarboxylate to give compounds of Formula I wherein X is $OR_5$ and $R_1$ is hydrogen.

Process 9

(i) Amides I, wherein Z is Br or I and produced by Process IV, were coupled with phenylacetylene under the aegis of tetrakis(triphenylphosphine) palladium(O) to give compounds of Formula I wherein Z is phenylacetylene.

(ii) Amides I, produced above, were hydrogenated over palladium on carbon catalyst to produce compounds of Formula I wherein Z is hydrocinnamyl.

Process 10

(i) Amides I, wherein Z is I and produced by Process IV, were heated at reflux in pyridine in the presence of cuprous cyanide to produce compounds of Formula I wherein Z is cyano.

Process 11

(i) Amides I, wherein Z is I and produced by Process IV, were subjected to Mitsonobu coupling in the presence of aqueous barium hydroxide, phenylboric acid, tetrakis (triphenylphosphine) palladium(O) and dimethoxyethane to produce Formula I compounds wherein Z is phenyl.

Process 12 (Reactions a–h)

(i) Reduction via sodium borohydride of 3-methoxy cinnamic acid (XV), followed by sequential treatment with iodine and hydrochloric acid produced allylic alcohol XVI.

(ii) Compound XVI was acylated via acetic anhydride in pyridine to produce allylic acetate XVII.

(iii) Allylic acetate XVII was cyclopropanated via treatment with sodium chlorodifluoroacetate in refluxing diglyme to produce the difluorocyclopropane XVIII.

(iv) Difluorocyclopropane XVIII was treated with potassium hydroxide in methanol to give the corresponding alcohol XIX.

(v) Alcohol XIX was converted to a mesylate via treatment with methanesulfonyl chloride in dichloromethane in the presence of triethylamine. The mesylate was digested with dimethylformamide and treated with sodium azide to give the corresponding azide. The azide was reduced via lithium aluminum hydride to the amine XX.

(vi) Amine XX was converted to Amides I, wherein R is fluorine, by acylation with an acyl chloride in the presence of triethylamine.

Process 13 (Reactions a,b)

(i) Oxime XXI, produced as in Process II, was converted to diamine XXII via catalytic hydrogenation over palladium on carbon in acetic acid.

(ii) Diamine XXII was diacylated via treatment with two equivalents of an acyl chloride in the presence of triethylamine to give Amides I, wherein Z is alkamido.

Process 14 (Reactions a–d)

(i) Alcohol IX, produced via Process III, was oxidized via Swern oxidation to give the corresponding carboxaldehyde, which was treated with methyl magnesium bromide to give a mixture of diastereomers. The epimers were separated by chromatography to produce pure alcohols XXIII.

(ii) Alcohol XXIII was converted by treatment with phthalimide, diethylazo dicarboxylate, and triphenylphosphine to the phthalimide XXIV.

(iii) Phthalimide XXIV was treated with hydrazine in ethanol to give amine XXV.

(iv) Acylation of XXV was accomplished with an acyl chloride in the presence of triethylamine to give compounds of Formula I, wherein G is alkmethylene.

Process 15

(i) Phenol XIV, produced via Process VII, was converted to the sodium salt by treatment with sodium hydroxide and heated at reflux with ethylene carbonate in toluene to give Amides I, wherein $R_5$ is 2-hydroxyethyl.

Process 16 (Reactions a–c)

(i) Alcohol IX, produced via Process III, was treated with methanesulfonyl chloride in the presence of triethylamine to give a mesylate which was subsequently transformed, via treatment with sodium cyanide in dimethylformamide, to nitrile XXVI.

(ii) Nitrile XXVI was reduced with lithium aluminum hydride in tetrahydrofuran to give amine XXVII.

(iii) Amine XXVII was acylated with an acid chloride in the presence of triethylamine to give Amides I, wherein G is ethylene.

Process 17 (Reactions a–e)

(i) Commercially available 3-methoxycinnamic acid ethyl ester was cyclopropanated with the ylide derived from isopropyl triphenylphosphonium iodide and butyllithium to give cyclopropane XXVI.

(ii) Cyclopropane XXVI was converted to alcohol XXIX via reduction with lithium aluminum hydride in tetrahydrofuran.

(iii) Alcohol XXIX was treated with methanesulfonyl chloride and triethylamine in dichloromethane to produce a mesylate which was subsequently converted to azide XXX by treatment with sodium azide in dimethylformamide.

(iv) Azide XXX was reduced via lithium aluminum hydride in tetrahydrofuran to amine XXXI.

(v) Amine XXXI was acylated with an acyl halide and triethylamine to give Amides I, wherein R is methyl.

Reagents, solvents and reaction conditions for the above described preparative steps would be known to one skilled in the art of organic synthesis. All steps are conventional organic reactions having extensive precedent in the scientific literature.

These preparative methods may be varied in order to produce other compounds embraced by this invention but not specifically disclosed.

Additionally compounds of Formula I also encompass all pharmaceutically acceptable solvates, with hydrates being the preferred solvates. The present invention also includes geometrical isomers as well as optical isomers, e.g. mixtures of enantiomers as well as individual enantiomers and diastereomers, which arise as a consequence of structural asymmetry in certain compounds of the instant series. Trans-cyclopropane stereoisomers are in general preferred. Separation or stereospecific synthesis of the individual isomers is accomplished by application of various methods which are well known to practitioners in the art.

In addition, the invention includes isotopically labeled variants of the disclosed compounds, particularly radioiodinated compounds into which a radioactive isotope of iodine, such as $^{122}I$, $^{123}I$, $^{125}I$, or $^{131}I$, has been incorporated; such radiolabeled compounds are of utility as specific, high affinity receptors and thus can be employed in receptor binding assays, autoradiographic studies, and in other in vitro and in vivo biological tests which are used in the discovery and pharmacological characterization of novel melatonergic agents.

The "Description of Specific Embodiments" section hereinbelow provides greater descriptive details of the synthesis of compounds of Formula I and of intermediates of Formulas II–XXXI.

The compounds of the present invention have affinity for receptors of the endogenous pineal hormone, melatonin, as determined in a receptor binding assay, and exhibit agonist activity as determined by a functional assay. The biological tests are described below.

As is discussed above, melatonin is involved in the regulation of a variety of biological rhythms and exerts its biological effects via interaction with specific receptors. There is evidence that the administration of melatonin agonists is of clinical utility in the treatment of various conditions regulated by melatonin activity. Such conditions include depression, jet-lag, work-shift syndrome, sleep disorders, glaucoma, some disorders associated with reproduction, cancer, immune disorders and neuroendocrine disorders.

The systemic administration and dosing regimen of compounds of Formula I can be done in a manner similar to that described for melatonin itself. The dosage and dosage regimen must be adjusted using sound professional judgment and taking into consideration such variables as the age, body weight, sex and physical condition of the recipient, the route of administration and the nature of the illness being treated. Oral, transdermal, subcutaneous, intravenous, intramuscular, rectal, buccal, intranasal, and ocular routes of administration may be used.

One or more of the compounds of the invention is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatability, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate, mineral oil and the like. Mixtures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% of active compound(s) and 99.90 to 90%, or other suitable amounts, of excipient(s).

Dosage levels will be dictated by the patient's needs and by the medical judgment of the treating physician. Generally, however, dosages of about 0.1 mg to about 100 mg per day are useful to treat sleep, circadian rhythm or other medical disorders.

In methods of treatment employing the compounds of the invention, the treatment will involve the step(s) of administering one or more dosages of the compound to a host, preferably a mammalian, e.g. human host in need of such treatment.

DESCRIPTION OF SPECIFIC EMBODIMENTS

The compounds which constitute the present invention, their methods of preparation and their biological actions will appear more fully after consideration of the following examples, which are given for the purpose of illustration only and are not to be construed as limiting the invention's scope.

In the following examples, temperatures are expressed in degrees Celsius (°C.), hours are designated "h" or "hr", and melting points are uncorrected. The proton nuclear magnetic resonance (NMR) spectral characteristics refer to chemical shifts ($\delta$) expressed as parts per million (ppm) versus tetramethylsilane (TMS) as the reference standard. The relative area reported for NMR signals at various chemical shifts corresponds to the number of hydrogen atoms of a particular type in the molecule. The multiplicities of the signals are reported as broad singlet (br s), singlet (s), doublet (d), triplet (t) or multiplet (m). The NMR spectra were obtained using solutions of the compounds in either deuterodimethylsulfoxide (DMSO-$d_6$) or deuterochloroform (CDCl$_3$). Infrared (IR) spectral descriptions include only absorption wave numbers (cm-1) having functional group identification value and IR determinations were made using potassium bromide (KBr) as diluent. The elemental analyses are reported as percent by weight.

The following examples describe in detail the preparation of representative examples of compounds of Formula I and of synthetic intermediates. It will be apparent to those skilled in the art that modifications, both of material and methods, will allow preparation of other compounds disclosed herein. From the foregoing description and the following examples it is believed that one skilled in the art would be able to carry out the invention to the fullest extent.

EXAMPLES

Example 1

(Process 1)

Preparation of (trans)-N-[[2-(2-Fluoro-5-methoxyphenyl)cyclopropyl]methyl]-2-methylpropanamide Step i (a) (trans)-3-(2-Fluoro-5-methoxyphenyl)-2-propenenitrile: To a suspension of NaH (6.90 g, 60% dispersion in mineral oil, 173 mmol) in THF (500 mL) at 0° C. was added diethyl cyanomethylphosphonate (30.10 g, 170 mmol) dropwise. This was followed by the dropwise addition of a solution of 2-fluoro-5-methoxybenzaldehyde (24.5 g, 159 mmol) in THF (50 mL). The resulting suspension was allowed to warm to ambient temperature. After 18 h, $H_2O$ (200 mL) was added and the solution was extracted with EtOAc. The organics were combined, washed with brine, dried over $MgSO_4$, and concentrated to afford a white waxy solid. The material was then purified by Kügelrohr distillation to give the title compound, 24.3 g (86%): mp 56°-57° C.;
$^1$H NMR (300 MHz, $CDCl_3$) δ3.79 (s, 3H), 5.98 (d, J=16.1 Hz, 1H), 6.85–6.90 (m, 1H), 6.91–6.93 (m, 1H), 6.99 (t, J=6.5 Hz, 1H), 7.43 (d, J=16.1 Hz, 1H); MS (isobutane—DCI) m/e 177; Analysis calc'd for $C_{10}H_8NOF$: C, 67.79; H, 4.55; N, 7.91; found: C, 67.41; H, 4.44; N, 7.86.

(b) (trans)-2-(2-Fluoro-5-methoxyphenyl)cyclopropane carbonitrile: To a suspension of NaH (1.73 g, 72 mmol) in DMSO (40 mL) was added solid trimethylsulfoxonium iodide (15.9 g, 72 mmol) in small portions. After the foaming had subsided (40 min), a solution of (trans)-3-(2-fluoro-5-methoxyphenyl)-2-propenenitrile (4.26 g, 24 mmol) in DMSO (10 mL) was added dropwise, maintaining the temperature between 35°–40° C. Stirring was continued for 18 h at room temperature, followed by the dropwise addition of saturated $NH_4Cl$ (100 mL) and extraction with ethyl acetate. The organics were combined, washed with brine, dried ($K_2CO_3$), and concentrated to give a red oil which was then purified by silica gel chromatography ($CH_2Cl_2$/hexane, 60:40) to afford the title compound as a clear oil (46% yield): $^1$H NMR (300 MHz, $CDCl_3$) δ0.82–0.88 (m, 2H), 1.65–1.75 (m, 1H), 2.55–2.62 (m, 1H), 3.75 (s, 3H), 6.50–6.55 (m, 1H), 6.60–6.70 (m, 1H), 6.92 (t, J=6.5 Hz, 1H).

Step ii (c) (trans)-2-(2-Fluoro-5-methoxyphenyl)cyclopropanemethanamine: A suspension of (trans)-2-(2-fluoro-5-methoxyphenyl)cyclopropane carbonitrile (5.0 g, 26 mmol), $PtO_2$ (200 mg), and $CHCl_3$ (10 mL) in EtOH (65 mL) was hydrogenated in a Parr apparatus at 55 psi for 3 h. The catalyst was filtered through a plug of celite and the solvents were removed. The resulting hydrochloride salt was then partitioned between $CH_2Cl_2$ and 10% $K_2CO_3$. The organic layer was separated, dried over $K_2CO_3$, and concentrated to afford the title compound as the free amine, 3.8 g (74%): $^1$H NMR (250 MHz, $CDCl_3$) δ0.79–0.82 (m, 1H), 0.90–0.95 (m, 1H), 1.49 (br s, 2H), 1.70–1.76 (m, 1H), 1.82–1.86 (m, 1H), 2.60–2.74 (m, 2H), 3.75 (s, 3H), 6.35–6.42 (m, 1H), 6.50–6.62 (m, 1H), 6.85–6.90 (m, 1H).

(d) (trans)-N-[[2-(2-Fluoro-5-methoxyphenyl)cyclopropyl]methyl]-2-methylpropanamide:

To a magnetically stirred solution of (trans)-2-(2-fluoro-5-methoxyphenyl)cyclopropanemethanamine (600 mg, 3.1 mmol), $Et_3N$ (909 mg, 9.0 mmol), in dry dichloromethane (15 mL) at 0° C. was added isobutyryl chloride (352 mg, 3.3 mmol) dropwise. The resulting suspension was then allowed to warm to room temperature and stirred for 18 h. The solvents were removed and the residue was taken into EtOAc (100 mL) and washed sequentially with $H_2O$, 5% citric acid, 5% $K_2CO_3$, brine, and dried over $K_2CO_3$. Concentration by rotary evaporation yielded a crude oil which was then purified by Kügelrohr distillation. Recrystallization of the resultant solid from $Et_2O$/hexane (1:1) gave 380 mg (47% yield) of the title compound: mp 93°–94° C.; $^1$H NMR (300 MHz, $CDCl_3$) δ0.82–0.88 (m, 1H), 0.97–1.03 (m, 1H), 1.13 (d, J=8.1 Hz, 6H), 1.14–1.24 (m, 1H), 1.85–1.91 (m, 1H), 2.25–2.30 (m, 1H), 2.93–3.02 (m, 1H), 3.52 (dt, I=7.8, 13.8 Hz, 1H), 3.72 (s, 3H), 5.74 (br s, 1H), 6.41–6.44 (m, 1H), 6.59–6.64 (m, 1H), 6.91 (t, J=6.5 Hz, 1H); IR (NaCl Film) 3298, 2962, 1642, 1546, 1502, 1428 $cm^{-1}$; MS (isobutane—DCI) m/e 253; Analysis calc'd for $C_{15}H_{20}NO_2F$: C, 67.90; H, 7.60; N, 5.28; found: C, 68.18; H, 7.77; N, 5.24.

Example 2

(Process 2)

Preparation of (trans)-N-[[2-(3-Methoxyphenyl)cyclopropyl]methyl] butanamide

Step i (a)(b) (trans)-N-Methoxy-N-methyl-3-(3-methoxyphenyl)-2-propenamide: A solution of 3-methoxycinnamic acid (75.0 g, 0.42 mol) in thionyl chloride (250 mL) was heated at reflux for 1 h. The majority of the the thionyl chloride was then distilled off and the resulting residue was treated with dichloromethane and residual thionyl chloride was removed by codistillation to give 3-methoxycinnamic acid chloride of sufficient purity to be used without further purification. Pyridine (186 mL, 2.3 mol) and N,O-dimethylhydroxylamine hydrochloride (45.17 g, 0.46 mol) were added to a 0° C. solution of 3-methoxycinnamic acid chloride(0.42 mol) in dry dichloromethane (500 mL). The solution was stirred for 18 h at room temperature, diluted with dichloromethane (200 mL), and washed sequentially with 1N HCl, saturated sodium bicarbonate, and brine. It was then dried over $MgSO_4$ and concentrated in vacuo to give the title compound as a dark oil (88.43 g, 95%): $^1$H NMR (300 MHz, $CDCl_3$) δ3.25 (s, 3H), 3.68 (s, 3H), 3.84 (s, 3H), 6.82–6.86 (m, 1H), 7.00 (d, J=16.1 Hz, 1H), 7.10 (br s, 1H), 7.15–7.20 (m, 1H), 7.32 (t, J=6.6 Hz, 1H), 7.72 (d, J=16.0 Hz, 1H).

(c) (trans)-N-Methoxy-N-methyl-2-(3-methoxyphenyl)cyclopropanecarboxamide: To a suspension of NaH (16.27 g, 0.68 mol) in DMSO (375 mL) was added solid trimethylsulfoxonium iodide (149.16 g, 0.68 mol) in small portions. After the foaming had subsided (40 min), a solution of (trans)-N-methoxy-N-methyl-3-(3-methoxyphenyl)-2-propenamide (50 g, 0.23 mol) in DMSO (50 mL) was added dropwise, maintaining the temperature between 35°–40° C. Stirring was continued for 18 h at room temperature, followed by the dropwise addition of saturated $NH_4Cl$ (400 mL) and extraction with ethyl acetate. The organics were combined, washed with brine, dried ($K_2CO_3$), and concentrated to give a red oil which was then purified by Kügelrohr distillation (130° C., 0.5 mm Hg) to afford the title compound as a white wax (52.47 g, 100%): $^1$H NMR (300

MHz, CDCl₃) δ0.82–0.88 (m, 1H), 1.20–1.30 (m, 1H), 1.59–1.62 (m, 1H), 2.40–2.45 (m, 1H), 3.22 (s, 3H), 3.68 (s, 3H), 3.79 (s, 3H), 6.61–6.72 (m, 3H), 7.18 (t, J=6.0 Hz, 1H).

Step ii (d) (trans)-2-(3-Methoxyphenyl) cyclopropanecarboxaldehyde: To a rapidly stirred suspension of LiAlH₄ (7.74 g, 204 mmol) in THF (800 mL) at –45° C. was added a solution of the (trans)-N-methoxy-N-methyl-2-(3-methoxyphenyl)cyclopropanecarboxamide (40 g, 171 mmol) in THF (100 mL) maintaining the temperature below –40° C. by dropwise addition. After addition the cooling bath was removed and the reaction was allowed to warm to 5° C., then immediately recooled to –45° C. Potassium hydrogen sulfate (40 g, 300 mmol) in H₂O (120 mL) was cautiously added dropwise, the temperature maintained below –30° C. throughout. After addition the cooling bath was removed and the suspension was stirred at room temperature for 30 min. The mixture was filtered through celite and the filter cake was washed with ether. The combined filtrates were then washed with cold 1N HCl, 5% K₂CO₃, brine, and dried over MgSO₄. Concentration by rotary evaporation yielded the title compound as a clear oil (29.9 g, 99%): ¹H NMR (300 MHz, CDCl₃) δ1.49–1.58 (m, 1H), 1.65–1.73 (m, 1H), 2.10–2.19 (m, 1H), 2.58–2.67 (m, 1H), 3.80 (s, 3H), 6.66–6.78 (m, 3H), 7.21 (t, J=66 Hz, 1H), 9.32 (d, J=2.0 Hz, 1H).

Step iii (e)(f) (trans)-[2-(3-Methoxyphenyl) cyclopropanemethanamine: A solution of (trans)-2-(3-methoxyphenyl)cyclopropanecarboxaldehyde (31.0 g, 176 mmol), hydroxylamine hydrochloride (38.57 g, 555 mmol), ethanol (200 mL), water (120 mL), and 10N NaOH (55 mL, 555 mmol) was heated at reflux (steam bath) for 18 h. The solution was cooled to room temperature, diluted with water (1 L), washed sequentially with 1N HCl, H₂O, brine, and dried over K₂CO₃. Concentration by rotary evaporation produced 30.98 g (92%) of the oxime which was used directly in the next step. The oxime (30.98 g, 162 mmol) was digested with THF (50 mL) and added dropwise to a –45° C. suspension of LiAlH₄ (9.2 g, 242 mmol), in THF (300 mL) maintaining the temperature below –40° C. The reaction was then allowed to come to ambient temperature, stirred for 4 h, and recooled to –45° C. Potassium hydrogen sulfate (55 g, 404 mmol) in H₂O (200 mL) was then cautiously added dropwise. The cooling bath was removed and the suspension was stirred at room temperature for 30 min. The resulting paste was then filtered through celite, and the filter cake was washed with Et₂O. The combined filtrates were extracted with 1N HCl, the acid extracts were made basic (50% NaOH), and then extracted with dichloromethane. The organics were combined, washed with brine, dried (K₂CO₃), and concentrated in vacuo to give the title compound as a clear oil (17.62 g, 56%, two steps): ¹H NMR (300 MHz, CDCl₃) δ0.80–0.95 (m, 2H), 1.31–1.35 (m, 1H), 1.70–1.79 (m, 1H), 2.28 (br s, 2H), 2.70–2.74 (m, 2H), 3.79 (s, 3H), 6.60–6.71 (m, 3H), 7.17 (t, J=6.4 Hz, 1H).

Step iv (g) (trans)-N-[[2-(3-Methoxyphenyl)cyclopropyl]methyl]butanamide: To a magnetically stirred solution of (trans)-[2-(3-methoxyphenyl)cyclopropanemethanamine (1.02 g, 5.8 mmol) and Et3N (1.60 mL, 11.5 mmol) in dry dichloromethane (20 mL) at 0° C. was added butyryl chloride (0.69 g, 6.4 mmol) dropwise. The resulting suspension was allowed to warm to room temperature and stirred for 4 h. The solvents were removed and the residue was digested with EtOAc (100 mL) and washed sequentially with H₂O, 5% citric acid, 5% K₂CO₃, brine, and dried over K₂CO₃.

Concentration by rotary evaporation yielded a crude product which was then purified by flash chromatography (silica gel, 40% EtOAc/hexane) to afford 1.01 g (71%) of the title compound: ¹H NMR (300 MHz, CDCl₃) δ0.85–0.95 (m, 5H), 1.22–1.31 (m, 1H), 1.62 (q, J=7.1 Hz, 2H), 1.73–1.77 (m, 1H), 2.13 (t, J=7.7 Hz, 2H), 3.15–3.36 (m, 2H), 3.76 (s, 3H), 5.59 (s, 1H), 6.55–6.69 (m, 3H), 7.15 (t, J=6.5 Hz, 1H); IR (NaCl Film) 3302, 2862, 1732, 1644, 1464 cm⁻¹; MS (isobutane—DCI) m/e 247; Analysis calc'd for C₁₅H₂₁NO₂: C, 72.84; H, 8.56; N, 5.66; found: C, 72.71; H, 8.50; N, 5.62.

Example 3

(Process 3)

3a. Preparation of (+)-(trans)-N-[[2-(3-Methoxyphenyl)cyclopropyl]methyl]butanamide Step i (a) (+)-(trans)-2-(3-Methoxyphenyl) cyclopropanemethanol: To a suspension of LAH (0.65 g, 17.1 mmol) in THF (45 mL) at –45° C. was added a solution of (2'S)-N-(1S,2S)-2-(3-methoxyphenyl) cyclopropanecarbonyl] bornane-10',2'-sultam (3.36 g, 8.6 mmol), prepared according to the method of Vallgårda, J.; Appelberg, U.; Csöregh, I.; and Hacksell, U. (J. Chem. Soc. Perkin Trans. I, pages 461–470, 1994), in THF (20 mL) dropwise. The cooling bath was then removed and the reaction was allowed to warm to room temperature, followed by immediate recooling to –45° C. Potassium hydrogen sulfate (3.9 g, 29 mmol) in H₂O (15 mL) was cautiously added, allowing the temperature to rise to –5° C. The resulting paste was stirred at room temperature for 1 h, filtered through celite, and the filter cake was washed with Et₂O. The combined filtrates were washed with cold (0° C.) 1N HCl, 5% K₂CO₃, brine, dried (K₂CO₃), and concentrated to give a crude wax. Trituration with hexane, filtration of the precipitated chiral auxiliary, and subsequent concentration of the filtrate afforded the title compound as a clear oil (1.33 g, 87%): ¹H NMR (300 MHz, CDCl₃) δ0.90–1.00 (m, 2H), 1.21–1.25 (m, 1H), 1.52–1.59 (br s, 1H), 1.78–1.85 (m, 1H), 3.60 (dd, J=5.0, <1 Hz, 2H), 3.80 (s, 3H), 6.60–6.72 (m, 3H), 7.20 (t, J=7.5 Hz, 1H); [a]_D^{20} 55.5° C. (c=1, CH₂Cl₂).

Step ii (b)(c) (+)-(trans)-1-(Azidomethyl)-2-(3-methoxyphenyl) cyclopropane: To a solution of (+)-(trans)-2-(3-methoxyphenyl)cyclopropanemethanol (1.33 g, 7.5 mmol) and triethylamine (1.57 mL, 11.3 mmol) in dichloromethane (25 mL) at 0° C. was added methanesulfonyl chloride (950 mg, 8.3 mmol) dropwise. After addition was complete the ice bath was removed and stirring was continued for 30 min. The solution was treated with dichloromethane (100 mL), washed with H₂O, saturated NaHCO₃, and dried over K₂CO₃. Concentration by rotary evaporation gave 1.78 g of a crude oil. The mesylate was taken into DMF (25 mL), treated with sodium azide (980 mg, 15 mmol) and allowed to stir at room temperature for 18 h. The mixture was concentrated and the residue was taken into Et₂O, washed with H₂O, brine, and the solvents removed by rotary evaporation to produce 1.11 g (73%, two steps) of a clear oil: ¹H NMR (300 MHz, CDCl₃) δ0.85–0.92 (m, 2H), 1.41–1.45 (m, 1H), 1.80–1.83 (m, 1H), 3.25–3.38 (m, 1H), 3.48–3.58 (m, 1H), 3.83 (s, 3H), 6.70–6.78 (m, 3H), 7.21 (t, J=7.8 Hz, 1H).

(d) (+)-(trans)-2-(3-Methoxyphenyl) cyclopropanemethanamine: To a stirred suspension of LAlH₄ (455 mg, 12 mmol) in THF (20 mL) at –30° C. was added a solution of (+)-(trans)-1-(azidomethyl)-2-(3-methoxyphenyl)cyclopropane (1.11 g, 5.5 mmol) in THF (10 mL). The temperature was maintained below -30° C., throughout. After addition was complete the suspension was allowed to warm to room temperature and stirred for 4 h. The reaction was cooled to -45° C. and a solution of KHSO$_4$ (2.6 g) in H$_2$O (20 mL) was cautiously added dropwise. The suspension was stirred at room temperature for 30 min, filtered through celite, and the filter cake was washed well with Et$_2$O. The filtrates were combined, extracted with 1N HCl and the acidic layers were basified (30%NaOH). The basic solution was extracted with CH$_2$Cl$_2$, dried (K$_2$CO$_3$), and concentrated to afford 400 mg (41%) of the title compound as a clear oil: $^1$H NMR (300 MHz, CDCl$_3$) δ0.86–0.95 (m, 2H), 1.24–1.31 (m, 1H), 1.72–1.79 (m, 1H), 2.10–2.40 (br s, 2H), 2.70–2.74 (m, 2H), 3.79 (s, 3H), 6.60–6.72 (m, 3H), 7.15 (t, J=7.8 Hz, 1H).

Step iii (e) (+)-(trans)-N-[[2-(3-Methoxyphenyl)cyclopropyl]methyl] butanamide: To a magnetically stirred solution of (+)-(trans)-2-(3-methoxyphenyl)cyclopropanemethanamine (400 mg, 2.3 mmol) and Et$_3$N (1.1 mL, 7.9 mmol) in dry dichloromethane (15 mL) at 0° C. was added butyryl chloride (269 mg, 2.5 mmol) dropwise. The resulting suspension was allowed to come to room temperature and stirred for 18 h. The solvents were removed and the residue was digested with EtOAc (100 mL) and washed sequentially with H$_2$O, 5% citric acid, 5% K$_2$CO$_3$, brine, and dried over K$_2$CO$_3$. Concentration by rotary evaporation yielded a crude product which was then purified by flash chromatography (silica gel, 1% MeOH/CH$_2$Cl$_2$) to afford 310 mg (56%) of the title compound as a clear oil: $^1$H NMR (300 MHz, CDCl$_3$) δ0.86–0.95 (m, 5H), 1.22–1.31 (m, 1H), 1.54–1.83 (m, 3H), 2.08 (t, J=7.7 Hz, 2H), 3.16–3.36 (m, 2H), 3.76 (s, 3H), 5.59 (br s, 1H), 6.55–6.76 (m, 3H), 7.17 (t, J=7.8 Hz, 1H); IR (NaCl Film) 3296, 2962, 1644, 1604, 1550, 1494 cm$^{-1}$; MS (isobutane—DCI) m/e 247; [a]$_D^{20}$ +57.2° (c=1, CH$_2$Cl$_2$); Analysis calc'd for C$_{15}$H$_{21}$NO$_2$.0.15 H$_2$O: C, 72.05; H, 8.59; N, 5.60; found: C, 71.97; H, 8.59; N, 5.60.

3b. (-)-(trans)-N-[[2-(3-Methoxyphenyl)cyclopropyl]methyl] butanamide: The title compound was synthesized by the above method from (2'R)-N-(1R,2R)-2-(3-methoxyphenyl)cyclopropanecarbonyl] bornane-10',2'-sultam, prepared according to the method of Vallgårda, J.; Appelberg, U.; Csöregh, L; and Hacksell, U. (*J. Chem. Soc. Perkin Trans. 1*, pages 461–470, 1994): $^1$H NMR (300 MHz, CDCl$_3$) δ0.86–0.95 (m, 5H), 1.22–1.31 (m, 1H), 1.54–1.83, (m, 3H), 2.08 (q, J=7.7 Hz, 2H), 3.16–3.36 (m, 2H), 3.76 (s, 3H), 5.59 (br s, 1H), 6.55–6.76 (m, 3H), 7.17 (t, J=7.8 Hz, 1H); IR (NaCl Film) 3294, 2962, 1644, 1604, 1550, 1494 cm$^{-1}$; MS (isobutane—DCI) m/e 247.

Example 4

(Process 4)

4a. Preparation of (trans)-N-[[2-(2-Iodo-5-methoxyphenyl)cyclopropyl]methyl]butanamide To a stirred solution of (trans)-N-[[2-(3-methoxyphenyl)cyclopropyl]methyl] butanamide (120 mg, 0.49 mmol) and Tl(OAc)$_3$ (522 mg, 1.5 mmol) in CCl$_4$ (10 mL) was added a solution of I$_2$ (139 mg, 0.55 mmol) in CCl$_4$ (20 mL). The resulting suspension was heated at reflux for 18 h. The suspension was cooled to ambient temperature, filtered through a medium pore glass frit, and the filtrate washed with saturated sodium thiosulfate, brine, and dried (K$_2$CO$_3$). Concentration by rotary evaporation gave 150 mg of an orange oil which was purified by chromatography (silica gel, 40% EtOAc/hexane) to afford 108 mg (60%) of the title compound as a white solid: mp 84°–86° C.; $^1$H NMR (300 MHz, CDCl$_3$) δ0.87–1.01 (m, 5H), 1.07–1.23 (m, 1H), 1.59–1.71 (m, 2H), 1.84–1.90 (m, 1H), 2.16 (t, J=7.8 Hz, 2H), 3.16–3.25 (m, 1H), 3.46–3.53 (m, 1H), 3.73 (s, 3H), 5.83 (br s, 1H), 6.45–6.50 (m, 2H), 7.66 (d, J=8.5 Hz, 1H); IR (NaCl Film) 3304, 2962, 1636, 1556, 1444, 1416 cm$^{-1}$; MS (isobutane—DCI) m/e 373; Analysis calc'd for C$_{15}$H$_{20}$NO$_2$I: C, 48.27; H, 5.40; N, 3.75; found: C, 48.24; H, 5.41; N, 3.53.

4b. Preparation of (trans)-N-[[2-(2-Iodo-5-fluorophenyl)cyclopropyl]methyl] butanamide To a stirred solution of (trans)-N-[[2-(3-fluorophenyl) cyclopropyl]methyl] butanamide (1.0 g, 4.3 mmol), Tl(OAc)$_3$ (2.5 g, 6.5 mmol), and TFA (15 mL) in acetonitrile (15 mL) was added a solution of NaI (705 mg, 4.7 mmol) in H$_2$O (2 mL). The resulting suspension was heated at 55° C. for 12 h. The suspension was cooled to ambient temperature, filtered through a medium pore glass frit, and the filtrate washed with saturated sodium thiosulfate, brine, and dried (K$_2$CO$_3$). Concentration by rotary evaporation gave 1.26 g of an orange oil which was purified by chromatography (silica gel, 35% EtOAc/hexane) to afford 371 mg (25%) of the title compound as a white solid: mp 66°–68° C.; $^1$H NMR (300 MHz, CDCl$_3$) δ0.91–0.99 (m, 5H), 1.00–1.15 (m, 1H), 1.70 (q, J=7.5 Hz, 2H), 1.89–1.92 (m, 1H), 2.17 (t, J=7.2 Hz, 2H), 3.28–3.32 (m, 1H), 3.43–3.50 (m, 1H), 5.67 (br s, 1H), 6.59–6.67 (m, 2H), 7.71–7.76 (m, 1H); IR (NaCl Film) 3417, 3294, 2962, 1638, 1554, 1448, 1412 cm$^{-1}$; MS (ESI) m/e 361; Analysis calc'd for C$_{14}$H$_{17}$NOFI: C, 46.55; H, 4.74, N, 3.88; found: C, 46.57; H, 4.68; N, 3.85.

Example 5

(Process 5)

Preparation of (trans)-N-[[2-(2,4-Dibromo-5-methoxyphenyl)cyclopropyl]methyl] butanamide To a stirred solution of N-[[2-(3-methoxyphenyl) cyclopropyl]methyl] butanamide (190 mg, 0.77 mmol), and Tl(OAc)3 (881 mg, 2.3 mmol) in CCl$_4$ (20 mL) at 0° C. was added a solution of Br2 (238 mg, 1.5 mmol) in CCl$_4$ (10 mL) dropwise. After addition was complete the suspension was filtered through a medium pore glass frit and the filtrate washed with saturated sodium thiosulfate, brine, dried (K$_2$CO$_3$) and concentrated to give a clear oil. Purification by chromatography (silica gel, 35% EtOAc/hexane) afforded 185 mg (62%) of the title compound as a white solid: m.p. 114°–115° C.; $^1$H NMR (300 MHz, CDCl$_3$) δ0.90–1.02 (m, 5H), 1.04–1.16 (m, 1H), 1.60–1.69 (m, 2H), 1.89–1.93 (m, 1H), 2.16 (t, J=7.8 Hz, 2H), 3.04–3.16 (m, 1H), 3.49–3.54 (m, 1H), 3.82 (s, 3H), 5.77 (br s, 1H), 6.44 (s, 1H), 7.66 (s, 1H); IR (NaCl Film) 3290, 2960, 1632, 1550, 1474, 1442 cm$^{-1}$; MS m/e 405; Analysis calc'd for C$_{15}$H$_{19}$NO$_2$Br$_2$: C, 44.47; H, 4.73; N, 3.46; found: C, 44.59; H, 4.65; N, 3.16.

Example 6

(Process 6)

Preparation of (trans)-N-[[2-(3-Methoxyphenyl) cyclopropyl]methyl]-N-(phenylmethyl) butanamide A magnetically stirred solution of (trans)-N-[2-[(3-methoxyphenyl)cyclopropyl]methyl] butanamide (1.0 g, 4.0 mmol) and NaH (105 mg, 4.4 mmol) in DMF (10 mL) was treated with benzyl bromide (750 mg, 4.4 mmol). The suspension was stirred for 18 h at room temperature, diluted with Et$_2$O (100 mL), and quenched with H$_2$O (100 mL). The layers were separated and the organic phase was washed with H$_2$O, brine, dried (K$_2$CO$_3$) and concentrated to give a crude oil which was purified by flash chromatography (silica gel, 45% EtOAc/Hexane) to afford 580 mg (43%) of the title compound as a clear oil: $^1$H NMR (300 MHz, CDCl$_3$) δ0.78–0.98 (m, 4H), 1.17–1.33 (m, 1H), 1.60–1.79 (m, 4H), 2.27–2.44 (m, 2H), 3.17–3.33 (m, 1H), 3.51–3.61 (m, 1H), 3.77 (br s, 3H), 4.46–4.82 (m, 2H), 6.50–6.72 (m, 3H), 7.10–7.34 (m, 6H); IR (NaCl Film) 2962, 1644, 1604, 1454, 1210 cm$^{-1}$; MS (isobutane—DCI) m/e 337; Analysis calc'd for C$_{22}$H$_{27}$NO$_2$.0.1 H$_2$O: C, 77.88; H, 8.08; N, 4.13; found: C, 77.87; H, 8.12; N, 3.89.

Example 7

(Process 7)

Preparation of (trans)-N-[[2-[3-(2-Propenyloxy) phenyl]cyclopropyl]methyl] butanamide Step i (a). (trans)-N-[[2-(3-Hydroxyphenyl)cyclopropyl] methyl] butanamide: To a stirred solution of (trans)-N-[[2-(3-methoxyphenyl)cyclopropyl]methyl]butanamide (3.50 g, 14.2 mmol) in dichloromethane (50 mL) at −78° C. was added BBr$_3$ (28.4 mL, 1N in CH$_2$Cl$_2$, 28.4 mmol) dropwise. After addition was complete, the cooling bath was removed and stirring was continued for 18 h. The solution was poured over ice/H$_2$O (100 mL) and extracted with 2.5N NaOH. The basic extracts were combined, washed with dichloromethane, and acidified (conc. HCl). The acidic solution was extracted with dichloromethane, the organics were combined, washed with brine, dried (MgSO$_4$), and concentrated to afford 2.49 g (75%) of the title compound: $^1$H NMR (300 MHz, DMSO-d$_6$)δ0.72–0.84 (m, 5H), 1.09–1.15 (m, 1H), 1.42–1.54 (m, 2H), 1.63–1.69 (m, 1H), 2.02 (t, J=5.0 Hz, 2H), 2.99–3.11 (m, 2H), 6.39–6.50 (m, 3H), 6.98 (t, J=7.8 Hz, 1H), 7.91 (s, 1H), 9.19 (br s, 1H); IR (NaCl Film) 3300, 2964, 1642, 1585, 1542, 1466 cm$^{-1}$; MS (isobutane—DCI) m/e 233; Analysis calc'd for C$_{14}$H$_{19}$NO$_2$.0.1 H$_2$O: C, 71.52; H, 8.23; N, 5.96; found: C, 71.53; H, 8.32; N, 5.92.

Step ii (b). (trans)-N-[[(2-Propen-1-yloxyphenyl)cyclopropyl] methyl] butanamide:

To a rapidly stirred solution of (trans)-N-[[2-(3-hydroxyphenyl)cyclopropyl]methyl] butanamide (0.8 g, 3.4 mmol) and KOH (210 mg, 3.74 mmol) in ethanol (15 mL) was added allyl iodide (622 mg, 3.7 mmol). After stirring for 18 h, the suspension was diluted with Et$_2$O (100 mL), and washed with H$_2$O, 2N NaOH, brine, dried (K$_2$CO$_3$), and concentrated to a give a crude residue. The resulting material was purified by chromatography (silica gel, 40 % EtOAc/hexane) to afford 320 mg (34%) of the title compound: $^1$H NMR (300 MHz, CDCl$_3$) δ0.70–0.94 (m, 5H), 1.12–1.32 (m, 1H), 1.58–1.84 (m, 3H), 2.20 (t, J=6.0 Hz, 2H), 3.15–3.36 (m, 2H), 4.48 (d, J=5.6 Hz, 2H), 5.24 (d, J=10.0 Hz, 1H), 5.40 (d, J=17.2 Hz, 1H), 5.56 (br s, 1H), 5.96–6.07 (m, 1H), 6.57–6.70 (m, 3H), 7.13 (t, J=7.2 Hz, 1H); IR (NaCl Film) 3296, 2962, 1644, 1607, 1548, 1494 cm$^{-1}$; MS m/e 273; Analysis calc'd for C$_{17}$H$_{23}$NO$_2$ 0.20(H$_2$O): C, 73.72; H, 8.52; N, 5.06; found: C, 73.77; H, 8.63; N, 5.00.

Example 8

(Process 8)

Preparation of (trans)-N-[[2-[3-(Methylethoxy) phenyl]cyclopropyl]methyl] butanamide To a rapidly stirred solution of (trans)-N-[[2-(3-hydroxyphenyl)cyclopropyl]methyl] butanamide (390 mg, 1.7 mmol), triphenylphosphine (498 mg, 1.9 mmol) and isopropanol (150 mg, 2.5 mmol) in THF (10 mL) at 0° C. was added diethyl azodicarboxylate (331 mg, 1.9 mmol) in one portion. After stirring for 2 h, the suspension was diluted with Et$_2$O (100 mL), washed with H$_2$O, 2N NaOH, and brine, dried (K$_2$CO$_3$) and concentrated to a give a crude wax. The resulting material was purified by chromatography (silica gel, 35% EtOAc/hexane) to afford 144 mg (31%) of the title compound: $^1$H NMR (300 MHz, CDCl$_3$) δ0.85–0.94 (m, 5H), 1.22–1.24 (m, 1H), 1.29 (d, J=6.7 Hz, 6H), 1.58–1.68 (m, 2H), 1.70–1.77 (m, 1H), 2.14 (t, J=6.0 Hz, 2H), 3.14–3.36 (m, 2H), 4.44–4.54 (m, 1H), 5.81 (br s, 1H), 6.53–6.67 (m, 3H), 7.13 (t, J=7.2 Hz, 1H); IR (NaCl Film) 3294, 2974, 1644, 1610, 1550, 1492 cm$^{-1}$; MS m/e 275; Analysis calc'd for C$_{17}$H$_{25}$NO$_2$: C, 74.14; H, 9.15; N, 5.09; found: C, 73.77; H, 8.99; N, 4.82.

Example 9

(Process 9)

9a. Preparation of (−)-(trans)-N-[[2-(5-Methoxy-2-phenylethynyl)phenyl]cyclopropyl]methyl] butanamide (a) (−)-(trans)-N-[[2-(5-Methoxy-2-phenylethynyl) phenyl]cyclopropyl]methyl] butanamide: A stirred suspension of (trans)-N-[[2-(2-iodo-5-methoxyphenyl) cyclopropyl] methyl] butanamide (400 mg, 1.1 mmol), phenyl acetylene (133 mg, 1.3 mmol), and Pd (Ph$_3$P)$_4$ (63 mg, 0.05 mmol) in triethylamine (10 mL) was heated at reflux for 18 h, cooled to ambient temperature, and diluted with Et$_2$O (100 mL), washed with H$_2$O, brine, dried (K$_2$CO$_3$), and concentrated in vacuo to give 400 mg of a red oil. Purification by chromatography (silica gel, 30% EtOAc/ Hexane) afforded 220 mg of a white solid (58%): mp 107°–108° C.; $^1$H NMR (300 MHz, CDCl$_3$) δ0.78 (t, J=7.5 Hz, 3H), 0.94–0.98 (m, 1H), 1.14–1.16 (m, 2H), 1.40–1.56 (m, 2H), 1.78–1.93 (m, 2H), 2.25–2.31 (m, 1H), 2.80–2.99 (m, 1H), 3.74–3.83 (m, 1H), 3.79 (s, 3H), 5.84 (br s, 1H), 6.41 (s, 1H), 6.71 (d, I=4 Hz, 1H), 7.16–7.61 (m, 6H); IR (NaCl Film) 3310, 2960, 2214, 1638, 1544, 1502, 1428 cm$^{-1}$; MS (ESI) m/e 347; Analysis calc'd for C$_{23}$H$_{25}$NO$_2$: C, 79.51; H, 7.25, N, 4.03; found: C, 79.28; H, 7.21; N, 3.78.

9b. Preparation of (−)-(trans)-N-[[2-(5-Methoxy-2-phenylethyl)phenyl]cyclopropyl]methyl] butanamide (b) (−)(trans)-N-[[2-(5-methoxy-2-phenylethyl)phenyl] cyclopropyl]methyl] butanamide: A suspension of (−)- (trans)-N-[[2-(5-methoxy-2-phenylethynyl)phenyl] cyclopropyl]methyl] butanamide (100 mg, 0.28 mmol), 10% Pd/C (50 mg) in ethanol (25 mL) was shaken under hydrogen (Parr apparatus, 50 psi) for 18 h. The suspension was filtered through celite and concentrated in vacuo to afford a clear oil (100 mg, 100%);

$^1$H NMR (300 MHz, CDCl$_3$) δ0.90–0.94 (m, 5H), 1.25–1.30 (m, 1H), 1.60–1.66 (m, 1H), 1.71–1.79 (m, 2H), 2.05–2.15 (m, 2H), 2.88–2.98 (m, 4H), 3.20–3.35 (m, 2H), 3.77 (s, 3H), 5.57 (br s, 1H), 6.47 (s, 1H), 6.66–6.68 (m, 1H), 7.05 (d, J=4 Hz, 1H), 7.17–7.32 (m, 5H); IR (NaCl Film) 3294, 2960, 1644, 1548, 1498, 1454 cm$^{-1}$; MS (ESI) m/e 351; Analysis calc'd for C$_{23}$H$_{29}$NO$_2$ 0.25(H$_2$O): C, 77.60; H, 8.41, N, 3.58; found: C, 77.48; H, 8.41; N, 3.58.

Example 10

(Process 10)

Preparation of (−)-(trans)-N-[[2-(2-Cyano-5-methoxyphenyl]cyclopropyl]methyl] butanamide To a 100 mL round bottom flask fitted with a reflux condenser equipped with a calcium chloride drying tube was added (trans)-N-[[2-(2-iodo-5-methoxyphenyl)cyclopropyl]methyl] butanamide (220 mg, 0.6 mmol), powdered copper (I) cyanide (106 mg, 1.2 mmol), and anhydrous pyridine (2 mL). The mixture was then heated at 185° C. for 18 h. The reaction was quenched by the addition of 50% aqueous ammonia solution (30 mL), followed by extraction with toluene (3×50 mL). The organics were combined, washed with $H_2O$, 1N HCl, brine, and dried over $MgSO_4$. Filtration and concentration in vacuo gave 310 mg of a crude oil which was further purified by chromatography (silica gel, 45% EtOAc/hexane) to afford a clear oil (120 mg, 74%): $^1H$ NMR (300 MHz, $CDCl_3$) δ0.93 (t, J=6.0 Hz, 3H), 0.96–0.99 (m, 1H), 1.10–1.16 (m, 1H), 1.20–1.28 (m, 1H), 1.64– 1.71 (m, 2H), 2.03–2.10 (m, 1H), 2.20 (t, J=7.8 Hz, 2H), 2.72–2.79 (m, 1H), 3.82 (s, 3H), 3.85–3.92 (m, 1H), 6.27 (br s, 1H), 6.56 (s, 1H), 6.73 (d, J=8.4 Hz, 1H), 7.53 (d, J=8.7 Hz, 1H); IR (NaCl Film) 3300, 2964, 2218, 1646, 1606, 1564, $cm^{-1}$; MS (ESI) m/e 272; Analysis calc'd for $C_{16}H_{20}N_2O_2$ 0.25($H_2O$): C, 69.41; H, 7.46, N, 10.12; found: C, 69.41; H, 7.46; N, 10.00.

Example 11

(Process 11)

Preparation of (−)-(trans)-N-[[2-(2-Phenyl-5-methoxyphenyl)cyclopropyl]methyl] butanamide To a stirred suspension of (trans)-N-[[2-(2-iodo-5-methoxyphenyl)cyclopropyl] methyl] butanamide (210 mg, 0.56 mmol), barium hydroxide (265 mg, 0.84 mmol), and $H_{20}$ (1 mL) in DME (6 mL) was added an admix of $Pd(Ph_3P)_4$ (12 mg, 0.01 mmol) and phenyl boronic acid (75 mg, 0.62 mmol) in one portion. The resulting mixture was then heated at reflux for 18 h, diluted with toluene, washed with $H_2O$, brine, dried over $K_2CO_3$ and concentrated in vacuo to give a red wax. Purification by chromatography (silica gel, 35% EtOAc/hexane) afforded 145 mg (85%) of clear oil: $^1H$ NMR (300 MHz, $CDCl_3$) δ0.69–0.76 (m, 1H), 0.89 (t, J=7.2 Hz, 3H), 0.93–0.98 (m, 1H), 1.01–1.08 (m, 1H), 1.51–1.64 (m, 2H), 1.79–1.86 (m, 1H), 2.01 (t, J=7.2 Hz, 2H), 2.78–2.86 (m, 1H), 3.21–3.30 (m, 1H), 3.79 (s, 3H), 5.04 (br s, 1H), 6.50 (s, 1H), 6.74 (d, J=8.4 Hz, 1H), 7.12 (d, J=8.5 Hz, 1H), 7.30–7.43 (m, 5H); IR (NaCl Film) 3296, 2962, 1644, 1610, 1550, 1482, $cm^{-1}$; MS (ESI) m/e 323; Analysis calc'd for $C_{21}H_{25}NO_2$ 0.5($H_2O$): C, 75.87; H, 7.88, N, 4.21; found: C, 75.95; H, 7.86; N, 4.15.

Example 12

(Process 12)

Preparation of (±)-(trans)-[2,2-Difluoro-3-(3-methoxyphenyl)cyclopropylmethyl] butanamide Step i (a) (±)-(trans)-3-(3-Methoxyphenyl)-prop-2-en-1-ol: A solution of 3-methoxycinnamic acid (50.24 g, 281 mmol) in 400 mL of anhydrous tetrahydrofuran was added to a magnetically stirred suspension of sodium borohydride (12.80 g, 338 mmol) in 500 mL of anhydrous tetrahydrofuran at room temperature. The suspension was stirred until gas evolution ceased, cooled to 0° C., and a solution of iodine (35.77 g, 141 mmol) in anhydrous tetrahydrofuran (500 mL) was added over 1 h. The suspension was stirred for 3 h and treated dropwise with a 4N solution of hydrochloric acid (100 mL). The resultant suspension was extracted with diethyl ether (3×500 mL), and the combined organic portions washed with 3N NaOH (3×500 mL), brine (500 mL), dried ($MgSO_4$), filtered, and concentrated in vacuo. Kügelrohr distillation (0.5 mm) gave the product as a clear liquid (23.12 g, 50%): $^1H$ NMR (300 MHz, $CDCl_3$) δ3.82 (s, 3H), 4.34 (d, J=6 Hz, 2H), 6.37 (dt, J=15, 6 Hz, 1H), 6.60 (d, J=15 Hz, 1H), 6.80 (dd, J=8, J=1 Hz, 1H), 6.93 (t, J=1 Hz, 1H), 7.00 (d, J=8 Hz, 1H), 7.24 (t, J=8 Hz, 1H).

Step ii (b) (±)-(trans)-Acetic acid (3-(3-methoxyphenyl) allyl ester: A magnetically stirred solution of (±)-(trans)-3-(3-Methoxyphenyl)-prop-2-en-1-ol (22.35 g, 136 mmol) in anhydrous pyridine (115 mL) at 0° C. was treated dropwise with acetic anhydride (16.0 mL, 170 mmol). After addition was complete the ice bath was removed, the solution was allowed to warm to room temperature, and stirred for 24 h. The solution was concentrated in vacuo and the residue digested with diethyl ether (300 mL), washed with 1N HCl (2×300 mL), 5% $NaHCO_3$ (200 mL), water (200 mL), brine (200 mL), dried over $MgSO_4$, filtered, and concentrated in vacuo to a clear liquid. Flash chromatography (5% diethyl ether/hexane elution) and Kügelrohr distillation (0.5 mm) of the resultant liquid gave the product as a clear liquid (16.95 g, 60%): $^1H$ NMR (300 MHz, $CDCl_3$) δ2.11 (s, 3H), 3.81 (s, 3H), 4.73 (d, J=6 Hz, 2H), 6.28 (dt, J=15, 6 Hz, 1H), 6.63 (d, J=15 Hz, 1H), 6.82 (dd, J=8, 1 Hz, 1H), 6.92 (t, J=1 Hz, 1H), 6.99 (d, J=8 Hz, 1H), 7.24 (t, J=8 Hz, 1H).

Step iii (c) (±)-(trans)-Acetic acid-2,2-difluoro-3-(3-methoxyphenyl)cyclopropyl methyl ester: A solution of (±)-(trans)-Acetic acid (3-(3-methoxyphenyl) allyl ester (1.63 g, 7.90 mmol) in anhydrous diglyme was heated at reflux and subsequently treated dropwise over 1 h with a solution of sodium chlorodifluoroacetate (9.02 g, 59.2 mmol) in anhydrous diglyme (25 mL). The suspension was cooled to room temperature and poured over 200 mL of ice. The resultant suspension was extracted with diethyl ether (4×200 mL) and the combined organic extracts were washed with water (3×400 mL), brine (400 mL), dried ($MgSO_4$), filtered, and concentrated in vacuo. Kügelrohr distillation (0.5 mm) gave 1.59 g (79%) of the product as a clear oil: $^1H$ NMR (300 MHz, $CDCl_3$) δ2.10 (s, 3H), 2.24 (ddt, J=15, 7.5, 7 Hz, 1 H), 2.63 (dd, J=15, 7.5 Hz, 1 H), 3.80 (s, 3H), 4.19–4.25 (m, 1H), 4.31–4.37 (m, 1H), 6.74–6.83 (m, 3H), 7.25 (t, J=8 Hz, 1H).

Step iv (d) (±)-(trans)-[2,2-Difluoro-3-(3-methoxyphenyl) cyclopropyl] methanol: A magnetically stirred solution of potassium hydroxide (2.39 g, 42.6 mmol) in 3:1 methanol/tetrahydrofuran (88 mL) was treated with (±)-(trans)-acetic acid-2,2-difluoro-3-(3-methoxyphenyl)cyclopropyl methyl ester (4.16 g, 16.2 mmol). The solution was stirred for 2 h and concentrated in vacuo. The residue was digested with diethyl ether (200 mL) and water (200 mL), the layers separated, the aqueous layer further extracted with diethyl ether (2×200 mL), the organic extracts washed with saturated $NaHCO_3$ solution (300 mL), water (300 mL), brine (300 mL), dried ($MgSO_4$), filtered, and concentrated in vacuo to give 3.42 g (99%) of a clear oil that was used without further purification: $^1H$ NMR (300 MHz, $CDCl_3$) δ1.60 (br s, 1H), 2.15–2.36 (m, 1 H), 2.60 (ddd, J=15, 7.5, 1.5 Hz, 1H), 3.81 (s, 3H), 3.83–3.98 (m, 2H), 6.77 (t, J=1 Hz, 1H), 6.81 (d, J=8 Hz, 1H), 6.82 (dd, J=8, 1 Hz, 1H), 7.26 (t, J=8 Hz, 1H).

Step v (e)(f)(g) (±)-(trans)-[2,2-Difluoro-3-(3-methoxyphenyl) cyclopropyl] methanamine: A magnetically stirred solution of the alcohol (3.27 g, 15.3 mmol), triethylamine (3.14 g, 31.0 mmol), and $CH_2Cl_2$ (50 mL) at 0° C. under nitrogen was treated dropwise over 15 min with methanesulfonyl chloride (2.8 g, 24.4 mmol). The solution was stirred 30 min, diluted with $CH_2Cl_2$ (200 mL), and washed sequentially with water (200 mL) and saturated $NaHCO_3$ (200 mL), dried ($K_2CO_3$), filtered, and concentrated in vacuo at 5° C. The residue was digested with anhydrous dimethylformamide (50 mL), treated with sodium azide (1.96 g, 30.1 mmol), and stirred 14 h. The resultant solution was poured into water (500 mL), extracted with diethyl ether (4×250 mL), the combined extracts washed with water (4×500 mL), brine (2×300 mL), dried ($MgSO_4$), filtered, and concentrated in vacuo (caution!) to a clear oil. The oil was digested with anhydrous diethyl ether (40 mL) and added dropwise to a magnetically stirred suspension of lithium aluminum hydride (1.16 g, 30.6 mmol) in anhydrous diethyl ether (60 mL) at −30° C. The suspension was allowed to warm to room temperature, stirred for 3 h, recooled to −30° C., and treated dropwise with a solution of $KHSO_4$ (2.6 g, 19 mmol) in water (20 mL). The resultant suspension was allowed to warm to room temperature, stirred 1 h, and filtered through celite with diethyl ether elution (400 mL). The layers were separated and the organic layer extracted with 1N HCl (3×100 mL), the combined aqueous extracts made basic with 50% NaOH, and extracted with $CH_2Cl_2$ (3×150 mL). The organic portion was washed with brine (200 mL), dried ($K_2CO_3$), filtered, and concentrated in vacuo to give 1.23 g (38%) of a clear oil: $^1$H NMR (300 MHz, $CDCl_3$) δ1.42 (br s, 2H), 1.97–2.08 (m, 1 H), 2.44–2.52 (m, 1H), 2.91–3.10 (m, 2H), 3.80 (s, 3H), 6.76 (t, J=1 Hz, 1H), 6.81 (d, J=8 Hz, 1H), 6.81 (dd, J=8, 1 Hz, 1H), 7.23 (t, J=8 Hz, 1H).

Step vi (h) (−)-(trans)-[2,2-Difluoro-3-(3-methoxyphenyl) cyclopropylmethyl] butanamide: A magnetically stirred solution of (−)-(trans)-[2,2-Difluoro-3-(3-methoxyphenyl)-cyclopropyl] methanamine (672 mg, 3.16 mmol) and triethylamine (1.5 mL) in anhydrous $CH_2Cl_2$ (20 mL) was treated dropwise with a solution of butyryl chloride (370 mg, 3.47 mmol) in anhydrous $CH_2Cl_2$ (3 mL). The solution was stirred for 48 h and concentrated in vacuo. The residue was digested with $CH_2Cl_2$ (100 mL) and washed with 1N HCl (100 mL), 1N NaOH (100 mL), brine (100 mL), dried ($K_2CO_3$), filtered, and concentrated in vacuo. Flash chromatography (2:1 hexanes/ethyl acetate elution) gave the product as a clear oil that solidified to a waxy solid on standing: $^1$H NMR (300 MHz, $CDCl_3$) δ0.92 (t, J=7.4 Hz, 3H), 1.64 (sextet, J=7.4 Hz, 2H), 2.09–2.21 (m, 1 H), 2.16 (t, J=7.4 Hz, 2H), 2.51 (dd, J=13.8, 7.4 Hz, 1H), 3.19–3.22 (m, 1 H), 3.76 (s, 3H), 3.77–3.85 (m, 1H), 5.90 (br s, 1H), 6.70 (s, 1H), 6.75 (d, J=8 Hz, 1H), 6.77 (dd, J=8, 1 Hz, 1H), 7.20 (t, J=8 Hz, 1H); IR (NaCl Film) 3302, 2960, 1644, 1552, 1288, 1266, 1250, 1160 cm$^{-1}$; MS (isobutane—DCI) m/e 282 (M—H$^-$); Analysis calc'd for $C_{15}H_{19}NO_2F_2$: C, 63.59; H, 6.76; N, 4.94; found: C, 63.59; H, 6.83; N, 4.85.

Example 13

(Process 13)

Preparation of (trans)-N-[[2-(2-Butyrylamino-5-methoxyphenyl)cyclopropyl]methyl] butanamide Step i (a) (trans)-N-[[2-(2-Amino-5-methoxyphenyl) cyclopropane] methyl] amine: A Parr bottle was charged with a suspension of (trans)-2-(2-nitro-5-methoxyphenyl) cyclopropane carboxaldehyde oxime (1.0 g, 4.2 mmol), 10% Pd/C (100 mg) and HOAc (25 mL) was shaken under hydrogen (50 psi) for 18 h. The material was then filtered through celite, digested with $H_2O$ (300 mL) and made basic with 10N NaOH. The product was then extracted with $CH_2Cl_2$, the extracts were combined, dried over $K_2CO_3$, and concentrated in vacuo to afford 800 mg (100%) of a red oil: $^1$H NMR (300 MHz, $CDCl_3$) δ0.78–0.85 (m, 1H), 1.34–1.39 (m, 1H), 1.59–1.69 (m, 1H), 1.77–1.83 (m, 1H), 1.88 (br s, 2H), 3.10–3.38 (m, 2H), 3.66 (s, 3H), 6.39 (d, J=6.0 Hz, 1H), 6.50–6.59 (m, 1H), 6.61 (br s, 2H), 6.78 –6.97 (m, 1H).

Step ii (b) (trans)-N-[[2-(2-Butyryl amino-5-methoxyphenyl) cyclopropyl]methyl]butanamide: To a magnetically stirred solution of (trans)-N[[2-(2-amino-5-methoxyphenyl) cyclopropane]methyl]amine (400 mg, 2.2 mmol) and $Et_3N$ (0.86 mL, 6.6 mmol) in dry $CH_2Cl_2$ (15 mL) at 0° C. was added butyryl chloride (256 mg, 2.4 mmol) dropwise. The resulting suspension was allowed to come to room temperature and stirred for 18 h. Concentration by rotary evaporation yielded a crude product which was then purified by flash chromatography (silica gel, 30% EtOAc/hexane) to afford 250 mg (44% ) of a clear oil: $^1$H NMR (300 MHz, $CDCl_3$) δ0.75–1.04 (m, 8H), 1.50–1.76 (m, 5H), 2.10 (t, J=8.1 Hz, 2H), 2.45 (t, J=8.0 Hz, 2H), 2.68–2.78 (m, 1H), 3.69 (s, 3H), 3.72–3.78 (m, 2H), 6.27 (d, J=2.0 Hz, 1H), 6.36 (br s, 1H), 6.63 (dd, J=7.8, 2.7 Hz, 1H), 7.50 (d, J=8.7 Hz, 1H), 7.89 (br s, 1H); IR (NaCl Film) 3290, 2961, 1647, 1534, 1425 cm$^{-1}$; MS (ESI) m/e 332; Analysis calc'd for $C_{19}H_{28}N_2O_3$·0.4 $H_2O$: C, 67.19; H, 8.54; N, 8.24; found: C, 67.58; H, 8.19; N, 7.77.

Example 14

(Process 14)

Preparation of (−)-(trans)-N-1-[2-(3-Methoxyphenyl)cyclopropyl]ethyl] butanamide
(Isomer A)

Step i (a) (−)-(trans)-1-[2-(3-Methoxyphenyl)cyclopropyl] ethanol (Isomer A) and (−)(trans)-1-[2-(3-Methoxyphenyl) cyclopropyl] ethanol (Isomer B):

Dimethyl sulfoxide (3.98 mL, 56 mmol) was added dropwise to a solution of oxalyl chloride (2M in $CH_2Cl_2$, 19.5 mL, 39 mmol) in methylene chloride (20 mL) at −78° C. A solution of (−)-(trans)[2-(3-Methoxyphenyl) cyclopropyl] methanol (5.0 g, 28 mmol) in dichloromethane (10 mL) was added dropwise. The solution was stirred for 30 min, triethylamine (16.2 mL, 112 mmol) was slowly added, and the resulting suspension allowed to warm to room temperature. The suspension was stirred for 30 min, diluted with $CH_2Cl_2$ (100 mL), washed with water, dried over $K_2CO_3$, and concentrated in vacuo to afford 5.8 g of the aldehyde, which was used without purification The aldehyde was digested with THF (10 mL) and added dropwise to a solution of methyl magnesium bromide (3M in $Et_2O$, 23.3 mL, 70 mmol) in THF (25 mL) at 0° C. The solution was stirred at 0° C. for 2 h after which 2N HCl (20 mL) in EtOAc (250 mL) was added. The resultant suspension was then washed with $H_2O$, brine, dried ($K_2CO_3$), and concentrated in vacuo to give 5.5 g of a crude oil. Purification by silica gel chromatography (25% EtOAc/hexane) afforded two diastereomers, (isomer A) 1.66 g, 1st band, and (isomer B) 1.64 g, 2nd band: (isomer A) $R_f$=0.45 (25% EtOAc/hexanes); $^1$H NMR (300 MHz, $CDCl_3$) δ0.84–0.94 (m, 2H), 1.19–1.27 (m, 1H), 1.30 (d, J=6.3 Hz, 3H), 1.83–2.02 (m, 1H), 3.32–3.38 (m, 1H), 3.77 (s, 3H), 6.60–6.73 (m, 3H), 7.12 (t, J=7.8 Hz, 1H); $[a]_D^{20}$ −49.0° (c=1, $CH_2Cl_2$). (isomer B) $R_f$=0.40 (25% EtOAc/hexanes); $^1$H NMR (300 MHz, $CDCl_3$) δ0.93–1.00 (m, 2H), 1.21–1.29 (m, 1H), 1.32 (d, J=6.3 Hz, 3H), 1.75–1.78 (m, 1H), 3.33–3.38 (m, 1H), 3.77

(s, 3H), 6.59–6.69 (m, 3H), 7.15 (t, J=7.8 Hz, 1H); [a]$_D^{20}$ –55.3° (c=1, CH$_2$Cl$_2$).

Step ii (b) (–)-(trans)-2-[1-[2-(3-methoxyphenyl)cyclopropyl]ethyl]isoindole-1,3-dione (isomerA):

Diethyl azodicarboxylate (1.79 g, 10.3 mmol) was added dropwise to a stirred solution of (–)-(trans)-1-[2-(3-methoxyphenyl)cyclopropyl]ethanol (isomer A) (1.66 g, 8.6 mmol), triphenyl phosphine (2.69 g, 10.3 mmol), and phthalimide (1.52 g, 10.3 mmol) in THF (75 mL) at 0° C. The reaction was allowed to warm to ambient temperature and stirred for 18 h. The solvent was removed in vacuo and the resulting residue was digested with EtOAc (150 mL) and washed sequentially with 1N HCl, 1N NaOH, and brine. Drying over K$_2$CO$_3$, filtration, and concentration in vacuo afforded 2.6 g (94%) of the product as a waxy white solid: $^1$H NMR (300 MHz, CDCl$_3$) δ0.80–0.92 (m, 2H), 1.48–1.60 (m, 4H), 1.81–1.88 (m, 1H), 1.91–2.00 (m, 1H), 3.76 (s, 3H), 6.58–6.70 (m, 3H), 7.15 (t, J=7.8 Hz, 1H), 7.24–7.80 (m, 4H).

Step iii (c) (–)-(trans)-1-[2-(3-Methoxyphenyl)cyclopropyl]ethylamine (isomer A): A solution of (–)-(trans)-2-[1-[2-(3-methoxyphenyl)cyclopropyl]ethyl] isoindole-1,3-dione (isomer A) (2.6 g, 8.1 mmol) and hydrazine (827 mg, 25.8 mmol) in ethanol (75 mL) was stirred at room temperature for 18 h. The resultant white paste was diluted with ethanol (100 mL), treated with 10N HCl (10 mL), and stirred for 1 h. The solution was treated with EtOAc (200 mL), and extracted with 1N HCl. The acidic extracts were combined, washed with Et$_2$O, basified (10N NaOH), and extracted with CH$_2$Cl$_2$. The organics were dried over K$_2$CO$_3$ and concentrated in vacuo to give 1.1 g of a crude oil. Purification by silica gel chromatography (10% MeOH/CH$_2$Cl$_2$) afforded a clear oil (600 mg, 40%): $^1$H NMR (300 MHz, CDCl$_3$) δ0.85–0.98 (m, 2H), 1.10–1.20 (m, 1H), 1.25 (d, J=6.0 Hz, 3H), 1.70–1.79 (m, 1H), 2.30 (br s, 2H), 2.48–2.52 (m, 1H), 3.75 (s, 3H), 6.58–6.75 (m, 3H), 7.15 (t, J=7.0 Hz, 1H).

Step iv (d) (–)-(trans)-N-[1-[2-(3-Methoxyphenyl)cyclopropyl]ethyl] butanamide (isomer A): To a magnetically stirred solution of (–)-(trans)-1-[2-(3-methoxyphenyl)cyclopropyl]ethylamine (isomer A) (200 mg, 1.1 mmol) and Et$_3$N (0.46 mL, 3.3 mmol) in dry dichloromethane (15 mL) at 0° C. was added butyryl chloride (127 mg, 1.2 mmol) dropwise. The resulting suspension was allowed to warm to room temperature and stirred for 4 h. The solvent was removed in vacuo and the residue was digested with EtOAc (100 mL), washed sequentially with H$_2$O, 5% citric acid, 5% K$_2$CO$_3$, brine, and dried over K$_2$CO$_3$. Filtration and concentration in vacuo yielded a crude product which was then purified by flash chromatography (silica gel, 40% EtOAc/hexane) to afford 100 mg (39%) of the title compound: R$_f$=0.75 (10% MeOH/CHCl$_3$); $^1$H NMR (300 MHz, CDCl$_3$) δ0.85–0.97 (m, 4H), 1.04–1.17 (m, 2H), 1.24 (d, J=6.6 Hz, 3H), 1.61–1.73 (m, 2H), 1.77–1.83 (m, 1H), 2.19 (t, J=7.8 Hz, 2H), 3.54–3.68 (m, 1H), 3.77 (s, 3H), 5.59 (s, 1H), 6.57–6.71 (m, 3H), 7.15 (t, J=7.6 Hz, 1H); IR (NaCl Film) 3291, 2963, 1640, 1543, 1455 cm$^{-1}$; MS (ESI) m/e 261; Analysis calc'd for C$_{16}$H$_{23}$NO$_2$: C, 73.53; H, 8.87; N, 5.36; found: C, 73.48; H, 8.86; N, 5.25.

Example 15

(Process 15)

Preparation of (trans)-N-[[2-[3-(Methylethoxy)phenyl]cyclopropyl]methyl] butanamide A solution of (trans)-N-[[2-(3-hydroxyphenyl)cyclopropyl]methyl] butanamide (342 mg, 1.47 mmol) and sodium hydroxide (58 mg, 1.45 mmol) in anhydrous methanol (10 mL) was concentrated in vacuo and the residue powdered under anhydrous toluene (3 mL). The suspension was treated with a solution of ethylene carbonate (259 mg, 2.94 mmol) in anhydrous toluene (5 mL). The resultant mixture was heated at reflux for 12 h, cooled to room temperature, and treated with 3N NaOH (100 mL), ice (50 g), and diethyl ether (100 mL). The aqueous layer was separated and extracted with fresh diethyl ether (2×100 mL). The combined organic extracts were washed with water (200 mL), brine (200 mL), dried (K$_2$CO$_3$), filtered, and concentrated in vacuo. Flash chromatography of the resultant oil (1:2 hexane/ethyl acetate) gave 178 mg (44%)) of the compound as a clear oil: $^1$H NMR (300 MHz, CDCl$_3$) δ0.84–0.92 (m, 2H), 0.91 (t, J=7.4 Hz, 2H), 1.21–1.32 (m, 1H), 1.63 (sextet, J=7.4 Hz, 2H), 1.72–1.78 (m, 1H), 2.13 (t, J=7.4 Hz, 2H), 2.30 (br s, 1H), 3.16–3.34 (m, 2H), 3.91 (t, J=4.5 Hz, 2H), 4.03 (t, J=4.5 Hz, 2H), 5.75 (br s, 1H), 6.58 (t, J=1.5 Hz, 1H), 6.63 (d, J=8.0 Hz, 1H), 6.68 (ddd, J=8.0, 1.5, 1.5 Hz, 1 H), 7.13 (t, J=8.0 Hz, 1H); IR (NaCl Film) 3300, 3076, 2962, 1644, 1610, 1582, 1552 cm$^{-1}$; MS m/e 276 (M—H$^-$) ; Analysis calc'd for C$_{16}$H$_{23}$NO$_3$: C, 69.29; H, 8.36; N, 5.05; found: C, 68.99; H, 8.39; N, 4.93.

Example 16

(Process 16)

Preparation of (–)-(trans)-N-[[2-(3-Methoxyphenyl)cyclopropyl]ethyl]butanamide

Step i (a) (–)-(trans)-1-(Cyanomethyl)-2-(3-methoxyphenyl)cyclopropane: To a magnetically stirred solution of (–)-(trans)-2-(3-methoxyphenyl)cyclopropane methanol (1.60 g, 8.8 mmol) and triethylamine (1.9 mL, 13.2 mmol) in dichloromethane (150 mL) at 0° C. was added methanesulfonyl chloride (1.21 g, 10.6 mmol) dropwise. After addition was complete the ice bath was removed and stirring was continued for 1 h. The solution was treated with dichloromethane (150 mL), washed with saturated NaHCO$_3$, and dried over K$_2$CO$_3$. Concentration in vacuo gave 1.78 g of a crude oil which was utilized without further purification.

The mesylate was taken into DMF (100 mL), treated with sodium cyanide (862 mg, 17.6 mmol), and stirred on a steam bath for 4 h. The solution was concentrated in vacuo, the residue was taken into Et$_2$O (100 mL), washed with H$_2$O, brine, and the solvent removed in vacuo to produce 1.41 g (85%,) of a clear oil: $^1$H NMR (300 MHz, CDCl$_3$) δ0.90–1.09 (m, 2H), 1.23–1.30 (m, 1H), 1.81–1.92 (m, 1H), 2.52–2.60 (m, 2H), 3.78 (s, 3H), 6.58–6.72 (m, 3H), 7.19 (t, J=8.0 Hz, 1H).

(b) (–)-(trans)-2-(3-Methoxyphenyl)cyclopropane ethylamine: To a stirred suspension of LiAlH$_4$ (650 mg, 17 mmol) in THF (50 mL) at –45° C. was added a solution of (–)-(trans)-1-(cyanomethyl)-2-(3-methoxyphenyl)cyclopropane (1.41 g, 7.5 mmol) in THF (25 mL). The temperature was maintained below –30° C., throughout. After addition was complete, the suspension was allowed to warm to room temperature and stirred for 4 h. The suspension was recooled to –45° C. and 1N HCl (50 mL) was cautiously added dropwise. The suspension was stirred at room temperature for 30 min, filtered through celite, and the filter cake was washed well with Et$_2$O. The filtrates were combined, extracted with 1N HCl, and the acidic layers were basified (30% NaOH). The basic solution was extracted with CH$_2$Cl$_2$, dried (K$_2$CO$_3$), and concentrated in vacuo to afford 500 mg (39%) of a clear oil: $^1$H NMR (300 MHz, CDCl$_3$) δ0.75–0.82 (m, 1H), 0.88–0.96 (m, 1H), 1.00–1.11 (m, 1H), 1.45–1.70 (m, 3H), 2.62 (br s, 2H), 2.88 (t, J=7.5 Hz, 2H), 3.77 (s, 3H), 6.52–6.70 (m, 3H), 7.18 (t, J=8.0 Hz, 1H).

(c) (−)-(trans)-N-[[2-(3-Methoxyphenyl)cyclopropyl] ethyl] butanamide: To a magnetically stirred solution of (−)-(trans)-2-(3-methoxyphenyl) cyclopropane ethylamine (400 mg, 2.2 mmol) and Et$_3$N (0.86 mL, 6.6 mmol) in dry dichloromethane (15 mL) at 0° C. was added butyryl chloride (256 mg, 2.4 mmol) dropwise. The resulting suspension was allowed to come to room temperature and stirred for 18 h. Concentration in vacuo yielded a crude product which was then purified by flash chromatography (silica gel, 30% EtOAc/hexane) to afford 250 mg (44%) of a clear oil: $^1$H NMR (300 MHz, CDCl$_3$) δ0.70–0.81 (m, 1H), 0.88–1.01 (m, 5H), 1.54–1.68 (m, 5H), 2.12 (t, J=7.2 Hz, 2H), 3.29–3.36 (m, 2H), 3.77 (s, 3H), 5.75 (br s, 1H), 6.54–6.71 (m, 3H), 7.14 (t, J=7.8 Hz, 1H); IR (NaCl Film) 3295, 2962, 1644, 1604, 1551, 1494 cm$^{-1}$; MS (ESI) m/e 261; [a]$_D^{20}$ −66.3 (c=1, CH$_2$Cl$_2$); Analysis calc'd for C$_{16}$H$_{23}$NO$_2$.0.20 H$_2$O: C, 72.53; H, 8.90; N, 5.29; found: C, 72.67; H, 9.03; N, 5.29.

Example 17

(Process 17)

Preparation of (trans)-N-[[3-(3-methoxyphenyl)-2,2-dimethyl-1-cyclopropyl]methyl]butanamide.

Step i (a) (trans)-3-(3-Methoxyphenyl)-2,2-dimethyl-cyclopropane carboxylic acid ethyl ester: To a stirred solution of isopropyltriphenylphosphonium iodide (50 g, 116 mmol) in THF (250 mL) at 0° C. was added butyllithium (2.3M in hexane, 42.2 mL, 115.6 mmol) dropwise, maintaining the temperature below 5° C. throughout. The solution was stirred for 1 h, treated dropwise with a solution of cinnamic acid ethyl ester (18.33 g, 89 mmol) in THF (50 mL), allowed to warm to room temperature, and stirred for 4 h. The resulting suspension was quenched with saturated NH$_4$Cl (200 mL), and extracted with ethyl acetate. The organic extracts were combined, washed with brine, dried (K$_2$CO$_3$), and concentrated to give a light brown solid. This solid was then purified by Kügelrohr distillation (110° C., 0.5 mm) to give 13.0 g (59%) of a clear oil: $^1$H NMR (300 MHz, CDCl$_3$) δ0.95 (s, 3H), 1.12 (t, J=8.5 Hz, 3H), 1.38 (s, 3H), 1.95 (d, J=6.0 Hz, 1H), 2.62 (d, J=6.0 Hz, 1H), 3.80 (s, 3H), 4.12 (q, J=7.0 Hz, 2H), 6.65–6.68 (m, 2H), 7.18–7.26 (m, 2H).

Step ii (b) (trans)-(3-(3-Methoxyphenyl)-2,2-dimethyl-cyclopropyl) methanol: To a suspension of LiAlH$_4$ (4.21 g, 111 mmol) in THF (200 mL) at −45° C. was added a solution of (trans)-3-(3-methoxyphenyl)-2,2-dimethyl-cyclopropane carboxylic acid ethyl ester (12.5 g, 50.4 mmol) in THF (20 mL) dropwise. The cooling bath was then removed and the reaction was allowed to come to room temperature followed by immediate recooling to −45° C. A solution of KHSO$_4$ (24 g, 177 mmol) in H$_2$O (50 mL) was cautiously added allowing the temperature to rise to −5° C. The resulting paste was stirred at room temperature for 1 h, filtered through celite, and the filter cake was washed with Et$_2$O. The combined filtrates were washed with cold (0° C.) 1N HCl (3×), 5% K$_2$CO$_3$ (1×), brine (1×), dried (K$_2$CO$_3$), and concentrated to give 10.1 g (97%) of a clear oil: $^1$H NMR (300 MHz, CDCl$_3$) δ0.85 (s, 3H), 1.25 (s, 3H), 1.78 (d, J=6.0 Hz, 1H), 3.62–3.72 (m, 3H), 3.79 (s, 3H), 3.82 (dd, J=7, 10 Hz, 1H), 6.70–6.78 (m, 2H), 7.20 (t, J=7.5 Hz, 1H), 7.35 (m, 1H).

Step iii (c) (trans)-(3-(3-Methoxyphenyl)-2,2-dimethyl-cyclopropyl)methyl) azide: To a solution of (trans)-(3-(3-methoxyphenyl)-2,2-dimethyl-cyclopropyl) methanol (10.0 g, 48.5 mmol) and triethylamine (10.1 mL,72.8 mmol), in dichloromethane (100 mL) at 0° C. was added methanesulfonyl chloride (6.11 g, 53.4 mmol) dropwise. After addition was complete the ice bath was removed and stirring was continued for 30 min. The reaction was then diluted with dichloromethane (100 mL), washed with H$_2$O, saturated NaHCO$_3$, and dried over K$_2$CO$_3$. Concentration in vacuo gave 13.09 g of a colored oil suitable for use in the next step.

The above mesylate was taken into DMF (100 mL), treated with sodium azide (3.78 g, 58.2 mmol), and stirred at room temperature for 18 h. The mixture was concentrated and the residue was taken into Et$_2$O, washed with H$_2$O (1×), brine(1×), and the solvents removed in vacuo to produce 10.1 g of a clear oil suitable for use without further purification: $^1$H NMR (300 MHz, CDCl$_3$) δ0.85 (s, 3H), 1.30 (s, 3H), 1.39–1.42 (m, 1H), 1.80 (d, J=6.0 Hz, 1H), 3.30 (dd, J=8, 10 Hz, 1H), 3.51 (dd, J=6.0, 8.3 Hz, 1H), 3.80 (s, 3H), 6.68–6.79 (m, 3H), 7.20 (t, J=7.5 Hz, 1H).

Step iv (d) (trans)-(3-(3-Methoxyphenyl)-2,2-dimethyl-cyclopropyl)methyl) amine: A stirred suspension of LiAlH$_4$ (4.80 g, 126.6 mmol) in THF (100 mL) at −30° C. was treated with a solution of (trans)-(3-(3-methoxyphenyl)-2,2-dimethylcyclopropyl)methyl) azide (6.48 g, 30.14 mmol) in THF (10 mL), maintaining the temperature below −30° C. After addition was complete the suspension was allowed to come to room temperature and stirred for 4 h. The suspension was cooled to −45° C. and a solution of KHSO$_4$ (16 g) in H$_2$O (20 mL) was added dropwise (caution!). The resulting suspension was stirred at room temperature for 30 min, filtered through celite, and the filter cake was washed well with Et$_2$O. The filtrates were combined, extracted with 1N HCl (2×), and the acidic layers were basified (30% NaOH). The basic solution was extracted with CH$_2$Cl$_2$ (3×), dried (K$_2$CO$_3$), and concentrated to afford 2.80 g (47%) of a clear oil: $^1$H NMR (300 MHz, CDCl$_3$) δ0.82 (s, 3H), 1.22 (s, 3H), 1.60–1.68 (m, 4H), 2.75–2.92 (m, 2H), 3.78 (s, 3H), 6.68–6.75 (m, 3H), 7.15 (t, J=7.5 Hz, 1H).

Step v (e) (trans)-N-[[3-(3-methoxyphenyl)-2,2-dimethyl-1-cyclopropyl]methyl] butanamide: Acylation of (3-(3-methoxyphenyl)-2,2-dimethyl-cyclopropyl)methyl) amine (620 mg, 3.0 mmol) as in Example 1 was accomplished with butyryl chloride (0.34 mL, 3.3 mmol) to give 550 mg (67%) of a clear oil: $^1$H NMR (300 MHz, CDCl$_3$) δ0.80 (s, 3H), 0.90 (t, J=7.4 Hz, 3H), 1.23 (s, 3H), 1.23–1.30 (m, 1H), 1.58–1.71 (m, 3H), 2.14 (t, J=7.3 Hz, 2H), 3.39 (t, J=5.4 Hz, 2H), 3.76 (s, 3H), 5.50 (br s, 1H), 6.65–6.71 (m, 3H), 7.15 (t, J=7.8 Hz, 1H); IR (NaCl Film) 3294, 2964, 1642, 1550, 1490, 1456, 1274 cm$^{-1}$; MS m/e 275.39; Analysis calc'd for C$_{17}$H$_{25}$NO$_2$: C, 74.14; H, 9.15; N, 5.09; found: C, 73.95; H, 9.21;N, 5.11.

Table 1 shows chemical data for compounds of Formula I wherein X is OCH$_3$, R is hydrogen, G is methylene and the other substituents are as indicated below.

TABLE 1

[Structure: methoxy-phenyl ring with Y and Z substituents, cyclopropyl group, CH2-N(R1)-C(=O)-R2]

| Ex. No.* | Opt. Ism. | Prep. Process | Y | Z | R₁ | R₂ | Compound Formula | Elemental analysis Calc'd | Found |
|---|---|---|---|---|---|---|---|---|---|
| 1 | +/− | 1 | H | F | H | −CH(CH₃)₂ | C₁₅H₂₀NO₂F | C, 67.90; H, 7.60; N, 5.28 | C, 68.18; H, 7.77; N, 5.24 |
| 2 | +/− | 2 | H | H | H | −CH₂CH₂CH₃ | C₁₅H₂₁NO₂ | C, 72.84; H, 8.56; N, 5.66 | C, 72.71; H, 8.50; N, 5.62 |
| 3a | + | 3 | H | H | H | −CH₂CH₂CH₃ | C₁₅H₂₁NO₂·0.1H₂O | C, 72.31; H, 8.58; N, 5.62 | C, 72.30; H, 8.52; N, 5.59 |
| 3b | − | 3 | H | H | H | −CH₂CH₂CH₃ | C₁₅H₂₁NO₂ | C, 72.84; H, 8.56; N, 5.66 | C, 72.77; H, 8.52; N, 5.62 |
| 4 | +/− | 4 | H | I | H | −CH₂CH₂CH₃ | C₁₅H₂₀NO₂I | C, 48.27; H, 5.40; N, 3.75 | C, 48.24; H, 5.41; N, 3.53 |
| 5 | − | 5 | Br | Br | H | −CH₂CH₂CH₃ | C₁₅H₁₉NO₂Br₂ | C, 44.47; H, 4.73; N, 3.46 | C, 44.59; H, 4.65; N, 3.16 |
| 6 | +/− | 6 | H | H | Bn | −CH₂CH₂CH₃ | C₂₂H₂₇NO₂·0.1H₂O | C, 77.88; H, 8.08; N, 4.13 | C, 77.87; H, 8.12; N, 3.89 |
| 9a | + | 9a | H | Ph−C≡C− | H | −CH₂CH₂CH₃ | C₂₃H₂₅NO₂ | C, 79.51; H, 7.25; N, 4.03 | C, 79.28; H, 7.21; N, 3.78 |
| 9b | − | 9b | H | PhCH₂CH₂− | H | −CH₂CH₂CH₃ | C₂₃H₂₉NO₂·0.25(H₂O) | C, 77.60; H, 8.41; N, 3.58 | C, 77.48; H, 8.41; N, 3.58 |
| 10 | − | 10 | H | CN | H | −CH₂CH₂CH₃ | C₁₆H₂₀N₂O₂·0.25(H₂O) | C, 69.41; H, 7.46; N, 10.12 | C, 69.41; H, 7.46; N, 10.00 |
| 11 | − | 11 | H | Ph− | H | −CH₂CH₂CH₃ | C₂₁H₂₅NO₂·0.5(H₂O) | C, 75.87; H, 7.88; N, 4.21 | C, 75.95; H, 7.86; N, 4.15 |
| 13 | − | 13 | H | −NHCO(CH₂)₂CH₃ | H | −CH₂CH₂CH₃ | C₁₉H₂₈N₂O₃·0.4(H₂O) | C, 67.19; H, 8.54; N, 8.24 | C, 67.58; H, 8.19; N, 7.77 |
| 18 | +/− | 2 | H | H | H | −CH₂CH₃ | C₁₄H₁₉NO₂ | C, 72.07; H, 8.21; N, 6.00 | C, 71.83; H, 8.15; N, 5.80 |
| 19 | +/− | 2 | H | H | H | −CH₃ | C₁₃H₁₇NO₂ | C, 71.20; H, 7.81; N, 6.39 | C, 71.01; H, 7.77; N, 6.33 |
| 20 | +/− | 2 | H | H | H | −CH₂OCH₃ | C₁₄H₁₉NO₃ | C, 67.45; N, 7.68; N, 5.62 | C, 67.14; H, 7.85; N, 5.60 |
| 21 | +/− | 2 | H | H | H | −CH(CH₃)₂ | C₁₅H₂₁NO₂ | C, 72.84; H, 8.56; N, 5.66 | C, 72.64; H, 8.52; N, 5.61 |
| 22 | − | 3 | H | H | H | −CH(CH₃)₂ | C₁₅H₂₁NO₂ | C, 72.84; H, 8.56; N, 5.66 | C, 72.69; H, 8.50; N, 5.51 |
| 23 | +/− | 2 | H | H | H | −CH₂SCH₃ | C₁₄H₁₉NO₂S | C, 63.37; H, 7.22; N, 5.28 | C, 62.97; H, 7.05; N, 5.02 |
| 24 | +/− | 2 | H | H | H | −NH−CH₂CH₃ | C₁₄H₂₀N₂O₂·0.6H₂O | C, 64.89; H, 8.25; N, 10.81 | C, 64.81; H, 8.07; N, 10.67 |
| 25 | +/− | 2 | H | H | H | −CH₂CH₂CH₂CH₃ | C₁₆H₂₃NO₂·0.25H₂O | C, 72.28; H, 8.91; N, 5.27 | C, 72.01; H, 8.84; N, 5.22 |
| 26 | +/− | 2 | H | H | H | −CH₂CH(CH₃)₂ | C₁₆H₂₃NO₂·0.1H₂O | C, 73.02; H, 8.89; N, 5.32 | C, 72.92; H, 8.95; N, 5.22 |
| 27 | +/− | 2 | Cl | H | H | −CH₂CH₂CH₃ | C₁₅H₂₀NO₂Cl·0.1H₂O | C, 63.53; H, 7.18 | C, 63.40; H, 7.26 |

TABLE 1-continued

| Ex. No.* | Opt. Ism. | Prep. Process | Y | Z | R₁ | R₂ | Compound Formula | Elemental analysis Calc'd | Found |
|---|---|---|---|---|---|---|---|---|---|
| 28 | +/− | 2 | Cl | H | H | —NH—CH₂CH₃ | C₁₄H₁₉N₂O₂Cl | N, 4.94<br>C, 59.46<br>H, 6.77 | N, 4.86<br>C, 59.47<br>H, 6.69 |
| 29 | +/− | 2 | Cl | H | H | —CH₂OCH₃ | C₁₄H₁₈NO₃Cl.<br>0.5H₂O | N, 9.91<br>C, 57.43<br>H, 6.54 | N, 9.76<br>C, 57.46<br>H, 6.35 |
| 30 | +/− | 2 | Cl | H | H | —CH(CH₃)₂ | C₁₅H₂₀NO₂Cl | N, 4.78<br>C, 63.94<br>H, 7.15 | N, 4.54<br>C, 63.66<br>H, 7.12 |
| 31 | +/− | 4 | H | Br | H | —CH₂CH₂CH₃ | C₁₅H₂₀NO₂Br | N, 4.97<br>C, 55.22<br>H, 6.18 | N, 4.82<br>C, 55.28<br>H, 6.27 |
| 32 | +/− | 4 | H | I | H | —CH₂CH₂CH₃ | C₁₅H₂₀NO₂I | N, 4.29<br>C, 48.27<br>H, 5.40 | N, 4.22<br>C, 48.58<br>H, 5.14 |
| 33 | − | 4 | I | H | H | —CH₂CH₂CH₃ | C₁₅H₂₀NO₂I.<br>0.1(H₂O) | N, 3.75<br>C, 48.04<br>H, 5.43 | N, 3.63<br>C, 47.79<br>H, 5.44 |
| 34 | − | 11 | H | 4(CF₃)Ph— | H | —CH₂CH₂CH₃ | C₂₂H₂₄NO₂F₃.<br>0.75(H₂O) | N, 3.74<br>C, 65.25<br>H, 6.30 | N, 3.46<br>C, 64.85<br>H, 5.91 |
| 35 | − | 3 | H | H | H | —(CH₂)₂CH₂Cl | C₁₅H₂₀NO₂Cl | N, 3.46<br>C, 63.94<br>H, 7.15<br>N, 4.97 | N, 3.35<br>C, 63.62<br>H, 7.19<br>N, 4.88 |
| 36 | − | 3 | H | H | H | —CHCH₂CH₂ (ring) | C₁₅H₁₉NO₂ | C, 73.44<br>H, 7.81<br>N, 5.71 | C, 73.23<br>H, 7.70<br>N, 6.00 |
| 37 | − | 3 | H | H | H | —CHCH₂(CH₂)₂CH₂ (ring) | C₁₇H₂₃NO₂ | C, 74.69<br>H, 8.48<br>N, 5.12 | C, 74.61<br>H, 8.44<br>N, 5.08 |
| 38 | − | 3 | H | H | H | —CHCH₂CH₂CH₂ (ring) | C₁₆H₂₁NO₂ | C, 74.10<br>H, 8.16<br>N, 5.40 | C, 74.04<br>H, 8.19<br>N, 5.56 |
| 39 | − | 3 | H | H | H | —NHCH₃ | C₁₃H₁₈N₂O₂ | C, 66.64<br>H, 7.74<br>N, 11.96 | C, 66.48<br>H, 7.63<br>N, 11.93 |
| 40 | − | 3 | H | H | H | —CH₂CH₃ | C₁₄H₁₉NO₂ | C, 72.07<br>H, 8.21<br>N, 6.00 | C, 71.76<br>H, 8.37<br>N, 5.88 |
| 41 | − | 3 | H | H | H | —CH₃ | C₁₃H₁₇NO₂.<br>0.2(H₂O) | C, 70.05<br>H, 7.87<br>N, 6.28 | C, 70.05<br>H, 7.79<br>N, 6.35 |
| 42 | − | 3 | H | H | H | —CH₂CF₃ | C₁₄H₁₆NO₂F₃ | C, 58.53<br>H, 5.61<br>N, 4.88 | C, 58.74<br>H, 5.79<br>N, 4.78 |
| 43 | − | 3 | H | H | H | —CH₂CH₂CF₃ | C₁₅H₁₈NO₂F₃ | C, 59.79<br>H, 6.02<br>N, 4.65 | C, 60.02<br>H, 6.26<br>N, 4.58 |

Table 2 gives chemical data for the Formula I compounds wherein $R_1$ and R are hydrogen, G is methylene and $R_2$, X, Y, and Z are defined in the table.

TABLE 2

[Structure: X, Y substituted phenyl with Z, connected to cyclopropane-CH2-NH-C(=O)-R2]

| Ex. No. | Opt. Ism. | Prep. Proc. | X | Y | Z | R₂ | Compound Formula | Elemental analysis Calc'd | Found |
|---|---|---|---|---|---|---|---|---|---|
| 7a | ± | 7,8 | HO— | H | H | —CH₂CH₂CH₃ | C₁₄H₁₉NO₂·0.1H₂O | C, 71.52<br>H, 8.23<br>N, 5.96 | C, 71.53<br>H, 8.23<br>N, 5.92 |
| 7b | ± | 7 | CH₂=CHCH₂O— | H | H | —CH₂CH₂CH₃ | C₁₇H₂₃NO₂·0.2H₂O | C, 73.72<br>H, 8.52<br>N, 5.06 | C, 73.77<br>H, 8.63<br>N, 5.00 |
| 8 | ± | 8 | (CH₃)₂CHO— | H | H | —CH₂CH₂CH₃ | C₁₇H₂₅NO₂ | C, 74.14<br>H, 9.15<br>N, 5.09 | C, 73.77<br>H, 8.99<br>N, 4.82 |
| 15 | ± | 15 | HOCH₂CH₂O— | H | H | —CH₂CH₂CH₃ | C₁₆H₂₃NO₃ | C, 69.29<br>H, 8.36<br>N, 5.05 | C, 68.99<br>H, 8.39<br>N, 4.93 |
| 44 | ± | 3 | F— | H | H | —CH₂CH₂CH₃ | C₁₄H₁₈NOF | C, 71.46<br>H, 7.71<br>N, 5.95 | C, 71.29<br>H, 7.69<br>N, 6.02 |
| 45 | ± | 7 | Ph—(CH₂)₆—O— | H | H | —CH₂CH₂CH₃ | C₂₆H₃₅NO₂ | C, 79.35<br>H, 8.96<br>N, 3.56 | C, 78.95<br>H, 9.24<br>N, 3.53 |
| 46 | ± | 7 | Ph—(CH₂)₇—O— | H | H | —CH₂CH₂CH₃ | C₂₇H₃₇NO₂ | C, 79.56<br>H, 9.15<br>N, 3.44 | C, 79.57<br>H, 9.21<br>N, 3.33 |
| 47 | ± | 7 | Ph—C≡C(CH₂)₃—O— | H | H | —CH₂CH₂CH₃ | C₂₅H₂₉NO₂·0.75H₂O | C, 77.18<br>H, 7.90<br>N, 3.60 | C, 76.89<br>H, 7.54<br>N, 3.53 |
| 48 | ± | 7 | CH₃CH₂O— | H | H | —CH₂CH₂CH₃ | C₁₆H₂₃NO₂ | C, 73.53<br>H, 8.87<br>N, 5.36 | C, 73.45<br>H, 8.63<br>N, 5.16 |
| 49 | ± | 7 | CH₃(CH₂)₂O— | H | H | —CH₂CH₂CH₃ | C₁₇H₂₅NO₂ | C, 74.14<br>H, 9.15<br>N, 5.09 | C, 73.95<br>H, 9.01<br>N, 4.88 |
| 50 | ± | 7 | CH₃(CH₂)₃O— | H | H | —CH₂CH₂CH₃ | C₁₈H₂₇NO₂ | C, 74.70<br>H, 9.40<br>N, 4.84 | C, 74.63<br>H, 9.09<br>N, 4.67 |
| 51 | ± | 7 | CH₃(CH₂)₄O— | H | H | —CH₂CH₂CH₃ | C₁₉H₂₉NO₂ | C, 75.20<br>H, 9.63<br>N, 4.62 | C, 75.08<br>H, 9.67<br>N, 4.59 |
| 52 | ± | 7 | CH₃(CH₂)₅O— | H | H | —CH₂CH₂CH₃ | C₂₀H₃₁NO₂ | C, 75.66<br>H, 9.84<br>N, 4.41 | C, 75.61<br>H, 10.31<br>N, 4.41 |
| 53 | ± | 7 | CH₃(CH₂)₆O— | H | H | —CH₂CH₂CH₃ | C₂₁H₃₃NO₂ | C, 76.09<br>H, 10.03<br>N, 4.23 | C, 75.94<br>H, 9.99<br>N, 4.19 |
| 54 | ± | 7 | CH₃(CH₂)₇O— | H | H | —CH₂CH₂CH₃ | C₂₂H₃₅NO₂ | C, 76.47<br>H, 10.21<br>N, 4.05 | C, 76.30<br>H, 10.12<br>N, 3.80 |
| 55 | ± | 7 | CH₃(CH₂)₈O— | H | H | —CH₂CH₂CH₃ | C₂₃H₃₇NO₂ | C, 76.83<br>H, 10.37<br>N, 3.90 | C, 77.33<br>H, 10.33<br>N, 3.78 |
| 56 | ± | 7 | CH₃(CH₂)₉O— | H | H | —CH₂CH₂CH₃ | C₂₄H₃₉NO₂ | C, 77.16<br>H, 10.52<br>N, 3.75 | C, 77.09<br>H, 10.43<br>N, 3.66 |
| 57 | ± | 7 | CH₃(CH₂)₁₀O— | H | H | —CH₂CH₂CH₃ | C₂₅H₄₁NO₂ | C, 77.47<br>H, 10.66<br>N, 3.61 | C, 77.29<br>H, 10.70<br>N, 3.47 |
| 58 | ± | 7 | CH₃(CH₂)₁₁O— | H | H | —CH₂CH₂CH₃ | C₂₆H₄₃NO₂ | C, 77.75<br>H, 10.79<br>N, 3.49 | C, 77.70<br>H, 10.86<br>N, 3.39 |
| 59 | ± | 7 | CH₃(CH₂)₁₅O— | H | H | —CH₂CH₂CH₃ | C₃₀H₅₁NO₂ | C, 78.72<br>H, 11.23<br>N, 3.06 | C, 78.59<br>H, 11.20<br>N, 2.81 |
| 60 | ± | 7 | Ph—CH₂CH₂O— | H | H | —CH₂CH₂CH₃ | C₂₂H₂₇NO₂·0.25H₂O | C, 77.27<br>H, 8.11<br>N, 4.10 | C, 77.40<br>H, 8.02<br>N, 3.70 |
| 61 | ± | 7 | (CH₃)₂CHCH₂O— | H | H | —CH₂CH₂CH₃ | C₁₈H₂₇NO₂·0.1H₂O | C, 74.24<br>H, 9.42 | C, 74.22<br>H, 9.28 |

TABLE 2-continued

[Structure: X and Y on one side of benzene ring, Z on other, with cyclopropyl-CH2-NH-C(=O)-R2 substituent]

| Ex. No. | Opt. Ism. | Prep. Proc. | X | Y | Z | R$_2$ | Compound Formula | Elemental analysis Calc'd | Found |
|---|---|---|---|---|---|---|---|---|---|
| 62 | ± | 7 | 3(CH$_3$O)Ph(CH)$_2$O— | H | H | —CH$_2$CH$_2$CH$_3$ | C$_{24}$H$_{31}$NO$_3$ | N, 4.81<br>C, 75.56<br>H, 8.19 | N, 4.49<br>C, 75.21<br>H, 8.15 |
| 63 | ± | 8 | 4-Pyridyl(CH$_2$)$_3$O— | H | H | —CH$_2$CH$_2$CH$_3$ | C$_{22}$H$_{28}$N$_2$O$_2$·<br>0.25H$_2$O | N, 3.67<br>C, 74.02<br>H, 8.05 | N, 3.53<br>C, 73.93<br>H, 8.05 |
| 64 | — | 3 | CF$_3$O | H | H | —CH$_2$CH$_2$CH$_3$ | C$_{15}$H$_{18}$NO$_2$F$_3$ | N, 7.85<br>C, 59.79<br>H, 6.02 | N, 7.66<br>C, 59.81<br>H, 6.02 |
| 65 | — | 3 | F | H | H | —CH(CH$_3$)$_2$ | C$_{14}$H$_{18}$NOF | N, 4.65<br>C, 71.46<br>H, 7.71 | N, 4.60<br>C, 71.59<br>H, 7.75 |
| 66 | + | 4 | F | H | Br | —CH$_2$CH$_2$CH$_3$ | C$_{14}$H$_{17}$NOFBr | N, 5.95<br>C, 53.52<br>H, 5.45 | N, 5.87<br>C, 53.44<br>H, 5.52 |
| 67 | — | 4 | F | Br | H | —CH$_2$CH$_2$CH$_3$ | C$_{14}$H$_{17}$NOFBr | N, 4.46<br>C, 53.52<br>H, 5.45 | N, 4.42<br>C, 53.69<br>H, 5.56 |
| 68 | — | 4a | CF$_3$O | H | I | —CH$_2$CH$_2$CH$_3$ | C$_{15}$H$_{17}$NO$_2$F$_3$I | N, 4.46<br>C, 42.17<br>H, 4.01 | N, 4.43<br>C, 42.29<br>H, 3.95 |
| 69 | — | 4a | CF$_3$O | I | H | —CH$_2$CH$_2$CH$_3$ | C$_{15}$H$_{17}$NO$_2$F$_3$I | N, 3.28<br>C, 42.17<br>H, 4.01 | N, 3.21<br>C, 42.39<br>H, 4.07 |
| 70 | + | 4a | F | H | I | —CH$_2$CH$_2$CH$_3$ | C$_{14}$H$_{17}$NOFI | N, 3.28<br>C, 46.55<br>H, 4.74 | N, 3.25<br>C, 46.57<br>H, 4.68 |
| 71 | — | 4a | F | I | H | —CH$_2$CH$_2$CH$_3$ | C$_{15}$H$_{17}$NO$_2$F$_3$I·<br>0.1(EtOAc) | N, 3.88<br>C, 46.74<br>H, 4.85 | N, 3.85<br>C, 47.02<br>H, 4.77 |
| 72 | ± | 4a | CF$_3$O | H | Br | —CH$_2$CH$_2$CH$_3$ | C$_{15}$H$_{17}$NO$_2$F$_3$Br | N, 3.79<br>C, 47.39<br>H, 4.51 | N, 3.83<br>C, 47.18<br>H, 4.44 |
| 73 | ± | 2 | Br | H | H | —CH$_2$CH$_2$CH$_3$ | C$_{14}$H$_{18}$NOBr·<br>0.15(C$_6$H$_{12}$) | N, 3.68<br>C, 57.95<br>H, 6.46 | N, 3.66<br>C, 57.98<br>H, 6.34 |
| 74 | ± | 2 | Br | H | H | —CH$_3$ | C$_{12}$H$_{14}$NOBr·<br>0.1(C$_6$H$_{12}$) | N, 4.54<br>C, 54.72<br>H, 5.54 | N, 4.67<br>C, 54.85<br>H, 5.49 |
| 75 | ± | 2 | CH$_3$ | H | H | —CH$_2$CH$_2$CH$_3$ | C$_{15}$H$_{21}$NO·<br>0.15(H$_2$O) | N, 5.10<br>C, 76.98<br>H, 9.17 | N, 5.13<br>C, 76.86<br>H, 9.08 |
| 76 | ± | 2 | Br | H | H | —CH$_2$CH$_3$ | C$_{13}$H$_{16}$NOBr·<br>0.05(C$_6$H$_{12}$) | N, 5.99<br>C, 55.77<br>H, 5.85 | N, 6.35<br>C, 55.79<br>H, 5.92 |
| 77 | ± | 2 | CH$_3$ | H | H | —CH(CH$_3$)$_2$ | C$_{15}$H$_{21}$NO | N, 4.90<br>C, 77.88<br>H, 9.15 | N, 4.91<br>C, 77.83<br>H, 9.18 |
| 78 | ± | 2 | CH$_3$ | H | H | —CH$_3$ | C$_{13}$H$_{17}$NO·<br>0.1(H$_2$O) | N, 6.05<br>C, 76.13<br>H, 8.45 | N, 6.01<br>C, 75.76<br>H, 8.37 |
| 79 | — | 7a | HO | H | H | —CH$_2$CH$_2$CH$_3$ | C$_{14}$H$_{19}$NO$_2$·<br>0.2(H$_2$O) | N, 6.83<br>C, 70.97<br>H, 8.26 | N, 6.43<br>C, 71.04<br>H, 8.22 |
| 80 | ± | 2 | Cl | H | H | —CH$_2$CH$_2$CH$_3$ | C$_{14}$H$_{18}$NOCl·<br>0.1(H$_2$O) | N, 5.91<br>C, 66.31<br>H, 7.24 | N, 5.69<br>C, 66.53<br>H, 7.40 |
| 81 | ± | 2 | Cl | H | H | —CH$_2$CH$_3$ | C$_{13}$H$_{16}$NOCl·<br>0.1(H$_2$O) | N, 5.52<br>C, 65.19<br>H, 6.82 | N, 5.45<br>C, 65.12<br>H, 6.88 |
| 82 | ± | 2 | Cl | H | H | —CH$_3$ | C$_{12}$H$_{14}$NOCl·<br>0.15(H$_2$O) | N, 5.85<br>C, 63.66<br>H, 6.46<br>N, 6.19 | N, 5.76<br>C, 63.43<br>H, 6.53<br>N, 6.15 |

TABLE 2-continued

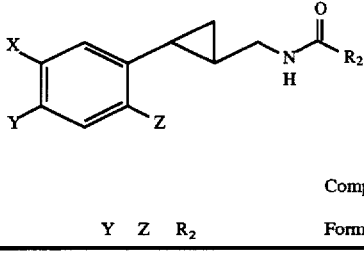

| Ex. No. | Opt. Ism. | Prep. Proc. | X | Y | Z | R₂ | Compound Formula | Elemental analysis Calc'd | Found |
|---|---|---|---|---|---|---|---|---|---|
| 83 | ± | 2 | Cl | H | H | —CHCH₂CH₂ (cyclic) | $C_{14}H_{16}NOCl$ | C, 67.33<br>H, 6.46<br>N, 5.61 | C, 67.28<br>H, 6.60<br>N, 5.43 |
| 84 | — | 7 | 3(CH₃O)Ph(CH₂)₃O— | H | H | —CH₂CH₂CH₃ | $C_{24}H_{31}NO_3$ | C, 75.56<br>N, 8.19<br>N, 3.67 | C, 75.36<br>H, 8.22<br>N, 3.59 |
| 85 | ± | 2 | F | H | F | —CH₃ | $C_{12}H_{13}NOF_2 \cdot 0.25(H_2O)$ | C, 62.73<br>H, 5.92<br>N, 6.10 | C, 62.75<br>H, 5.78<br>N, 6.05 |
| 86 | ± | 2 | F | H | F | —CH₂CH₃ | $C_{13}H_{15}NOF_2 \cdot 0.2(H_2O)$ | C, 64.29<br>H, 6.39<br>N, 5.77 | C, 64.22<br>H, 6.14<br>N, 5.72 |
| 87 | ± | 2 | F | H | F | —CH₂CH₂CH₃ | $C_{14}H_{17}NOF_2 \cdot 0.2(H_2O)$ | C, 65.45<br>H, 6.83<br>N, 5.45 | C, 65.61<br>H, 6.59<br>N, 5.39 |
| 88 | ± | 2 | F | H | F | —CHCH₂CH₂ (cyclic) | $C_{14}H_{15}NOF_2$ | C, 66.92<br>H, 6.02<br>N, 5.57 | C, 66.85<br>H, 6.08<br>N, 5.57 |
| 89 | — | 3 | CF₂CF₃ | H | H | —CH₂CH₂CH₃ | $C_{16}H_{18}NOF_5$ | C, 57.31<br>H, 5.41<br>N, 4.18 | C, 57.26<br>H, 5.57<br>N, 4.17 |
| 90 | — | 3a | H | H | H | —CH₂CH₂CH₃ | $C_{14}H_{19}NO \cdot 0.1(H_2O)$ | C, 76.38<br>H, 8.83<br>N, 6.45 | C, 76.87<br>H, 8.94<br>N, 6.39 |
| 91 | ± | 3a | H | H | H | —CH₃ | $C_{12}H_{15}NO$ | C, 76.16<br>H, 7.99<br>N, 7.40 | C, 75.99<br>H, 7.97<br>N, 7.39 |
| 92 | ± | 3a | H | H | H | —CH₂CH₂CH₃ | $C_{14}H_{19}NO \cdot 0.2(H_2O)$ | C, 76.12<br>H, 8.85<br>N, 6.34 | C, 76.08<br>H, 8.83<br>N, 6.33 |
| 93 | — | 7 | 3(CH₃O)Ph(CH₂)₃O— | H | I | —CH₂CH₂CH₃ | $C_{24}H_{30}NO_3I$ | C, 56.81<br>H, 5.96<br>N, 2.76 | C, 57.02<br>H, 6.03<br>N, 2.71 |
| 94 | ± | 7 | F(CH₂)₃O— | H | H | —CH₂CH₂CH₃ | $C_{17}H_{24}NO_2F \cdot 0.25H_2O$ | C, 68.54<br>H, 8.29<br>N, 4.70 | C, 68.48<br>H, 8.35<br>N, 4.63 |
| 95 | ± | 7 | Ph(CH₂)₃O— | H | H | —CH₂CH₂CH₃ | $C_{23}H_{29}NO_2$ | C, 78.60<br>H, 8.32<br>N, 3.98 | C, 78.32<br>H, 8.39<br>N, 3.85 |
| 96 | ± | 7 | PhO(CH₂)₃O— | H | H | —CH₂CH₂CH₃ | $C_{23}H_{29}NO_3$ | C, 75.17<br>H, 7.95<br>N, 3.81 | C, 74.92<br>H, 8.01<br>N, 3.70 |
| 97 | ± | 7 | PhO(CH₂)₄O— | H | H | —CH₂CH₂CH₃ | $C_{24}H_{31}NO_3$ | C, 75.56<br>H, 8.19<br>N, 3.67 | C, 75.30<br>H, 8.20<br>N, 3.53 |
| 98 | ± | 7 | 1-Pyrryl(CH₂)₃O— | H | H | —CH₂CH₂CH₃ | $C_{21}H_{28}N_2O_2 \cdot 0.25H_2O$ | C, 73.16<br>H, 8.28<br>N, 7.96 | C, 73.16<br>H, 8.28<br>N, 7.96 |
| 99 | ± | 7 | (CH₃)₂C=CH(CH₂)₂—<br>C(CH₃)=CHCH₂O— | H | H | —CH₂CH₂CH₃ | $C_{24}H_{35}NO_2$ | C, 78.00<br>H, 9.55<br>N, 3.79 | C, 77.74<br>H, 9.60<br>N, 3.55 |
| 100 | ± | 7 | (CH₃)₂C(CH₂)₄O— | H | H | —CH₂CH₂CH₃ | $C_{21}H_{33}NO_2 \cdot 0.25H_2O$ | C, 75.07<br>H, 10.05<br>N, 4.17 | C, 74.98<br>H, 9.98<br>N, 4.14 |
| 101 | ± | 7 | (CH₃)₂C=CH—<br>(CH₂)₂CH(CH₃)—<br>CH₂CH₂O— | H | H | —CH₂CH₂CH₃ | $C_{24}H_{37}NO_2 \cdot 0.25H_2O$ | C, 76.65<br>H, 10.05<br>N, 3.73 | C, 75.56<br>H, 10.04<br>N, 3.66 |
| 102 | ± | 7 | (CH₃)₂C=CH—<br>(CH₂)₂CH(CH₃)—<br>CH₂CH₂O— | H | H | —CH₂CH₂CH₃ | $C_{24}H_{37}NO_2$ | C, 77.58<br>H, 10.04<br>N, 3.77 | C, 77.40<br>H, 9.99<br>N, 3.63 |
| 103 | ± | 7 | (CH₃)₂C=CH—<br>(CH₂)₂C(CH₃)=<br>CH(CH₂)₂C(CH₃)=CH<br>CH₂O— | H | H | —CH₂CH₂CH₃ | $C_{29}H_{43}NO_2$ | C, 79.59<br>H, 9.90<br>N, 3.20 | C, 79.25<br>H, 9.92<br>N, 3.02 |

TABLE 2-continued

Structure: X and Y on one side of benzene ring, Z on other, attached to cyclopropyl-CH2-NH-C(=O)-R2

| Ex. No. | Opt. Ism. | Prep. Proc. | X | Y | Z | R₂ | Compound Formula | Elemental analysis Calc'd | Found |
|---|---|---|---|---|---|---|---|---|---|
| 104 | ± | 7 | (CH₃)₂C(CH₂)₂O— | H | H | —CH₂CH₂CH₃ | C₁₉H₂₉NO₂ · 0.25H₂O | C, 74.10; H, 9.66; N, 4.55 | C, 74.07; H, 9.51; N, 4.44 |
| 105 | ± | 7 | CH₂=CH(CH₂)₃O— | H | H | —CH₂CH₂CH₃ | C₁₉H₂₇NO₂ · 0.25H₂O | C, 74.59; H, 9.06; N, 4.61 | C, 74.49; H, 8.84; N, 4.61 |
| 106 | ± | 7 | (CH₃)₂C=CH(CH₂)₂O— | H | H | —CH₂CH₂CH₃ | C₂₀H₂₉NO₂ · 0.25H₂O | C, 75.08; H, 9.29; N, 4.38 | C, 75.15; H, 9.29; N, 4.26 |
| 107 | ± | 7 | NC(CH₃)₂C(CH₂)₄O— | H | H | —CH₂CH₂CH₃ | C₂₂H₃₂N₂O₂ · 0.3H₂O | C, 73.01; H, 9.08; N, 7.74 | C, 72.96; H, 9.08; N, 7.81 |
| 108 | ± | 7 | CH₃O₂C(CH₂)₃O— | H | H | —CH₂CH₂CH₃ | C₁₉H₂₇NO₄ | C, 73.01; H, 9.08; N, 7.74 | C, 72.96; H, 9.08; N, 7.81 |
| 109 | ± | 7 | Ph(CH₂)₄O— | H | H | —CH₂CH₂CH₃ | C₂₄H₃₁NO₂ · 0.25H₂O | C, 77.90; H, 8.58; N, 3.79 | C, 77.89; H, 8.47; N, 3.70 |
| 110 | ± | 7 | Ph(CH₂)₅O— | H | H | —CH₂CH₂CH₃ | C₂₅H₃₃NO₂ · 0.25H₂O | C, 78.18; H, 8.79; N, 3.64 | C, 78.13; H, 8.76; N, 3.60 |
| 111 | ± | 7 | CD₃O— | H | H | —CH₂CH₂CH₃ | C₁₅H₁₉NO₂D₃ | C, 70.59; H, 8.48; N, 5.56 | C, 70.20; H, 8.43; N, 5.39 |
| 112 | ± | 2 | CH₂CH₃ | H | H | —CH₃ | C₁₄H₁₉NO | C, 77.38; H, 8.81; N, 6.45 | C, 76.99; H, 9.04; N, 6.46 |
| 113 | ± | 2 | CH₂CH₃ | H | H | —CH₂CH₃ | C₁₅H₂₁NO | C, 77.88; H, 9.15; N, 6.05 | C, 77.55; H, 9.39; N, 5.99 |
| 114 | ± | 2 | CH₂CH₃ | H | H | —CH₂CH₂CH₃ | C₁₆H₂₃NO | C, 78.32; H, 9.45; N, 5.71 | C, 778.40; H, 9.69; N, 5.71 |
| 115 | ± | 2 | CH₂CH₃ | H | H | —CHCH₂CH₂ (cyclic) | C₁₆H₂₁NO | C, 78.32; H, 9.45; N, 5.71 | C, 78.57; H, 8.86; N, 5.68 |
| 116 | ± | 8 | cyclohexyl(CH₂)₄O— | H | H | —CH₂CH₂CH₃ | C₂₄H₃₇NO₂ · 0.1H₂O | C, 77.21; H, 10.04; N, 3.75 | C, 76.96; H, 10.27; N, 3.93 |
| 117 | ± | 8 | cyclohexyl(CH₂)₃O— | H | H | —CH₂CH₂CH₃ | C₂₃H₃₅NO₂ · 0.1H₂O | C, 76.88; H, 9.88; N, 3.90 | C, 76.81; H, 10.02; N, 4.20 |
| 118 | ± | 8 | CH₃CH₂(CH₃)CH—(CH₂)₂O— | H | H | —CH₂CH₂CH₃ | C₂₀H₃₁NO₂ · 0.25H₂O | C, 74.61; H, 9.86; N, 4.35 | C, 74.22; H, 9.82; N, 4.62 |
| 119 | ± | 8 | (CH₃)₂C(CH₂)₃CH—(CH₃)(CH₂)₂O— | H | H | —CH₂CH₂CH₃ | C₂₄H₃₉NO₂ · 0.1H₂O | C, 76.79; H, 10.53; N, 3.73 | C, 76.70; H, 10.89; N, 3.81 |
| 120 | ± | 8 | cyclopentyl(CH₂)₃O— | H | H | —CH₂CH₂CH₃ | C₂₂H₃₃NO₂ · 0.25H₂O | C, 75.93; H, 9.70; N, 4.03 | C, 75.68; H, 9.63; N, 4.15 |
| 121 | ± | 8 | (CH₃)₃CCH₂CH—(CH₃)CH₂CH₂O— | H | H | —CH₂CH₂CH₃ | C₂₃H₃₇NO₂ | C, 76.83; H, 10.37; N, 3.90 | C, 76.60; H, 10.52; N, 3.92 |
| 122 | ± | 8 | HC≡CC(CH₃)=CH—CH₂O— | H | H | —CH₂CH₂CH₃ | C₂₀H₂₅NO₂ · 0.2(CH₂Cl₂) | C, 74.07; H, 7.55; N, 4.60 | C, 74.24; H, 7.74; N, 4.23 |
| 123 | ± | 8 | 3(CF₃)Ph(CH₂)₂O— | H | H | —CH₂CH₂CH₃ | C₂₃H₂₆NO₂F₃ | C, 68.13; H, 6.46; N, 3.45 | C, 67.89; H, 6.51; N, 3.55 |
| 124 | ± | 8 | 2(CF₃)Ph(CH₂)₂O— | H | H | —CH₂CH₂CH₃ | C₂₃H₂₆NO₂F₃ · 0.1H₂O | C, 67.83; H, 6.44; N, 3.44 | C, 67.58; H, 6.44; N, 3.46 |
| 125 | ± | 8 | 3(F)Ph(CH₂)₂O— | H | H | —CH₂CH₂CH₃ | C₂₂H₂₆NO₂F | C, 73.41 | C, 73.10 |

TABLE 2-continued

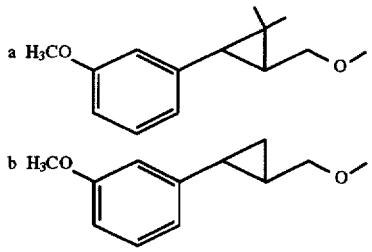

| Ex. No. | Opt. Ism. | Prep. Proc. | X | Y | Z | R₂ | Compound Formula | Elemental analysis Calc'd | Found |
|---|---|---|---|---|---|---|---|---|---|
|  |  |  |  |  |  |  | 0.25H₂O | H, 7.42<br>N, 3.89 | H, 7.44<br>N, 4.11 |
| 126 | ± | 8 | 2,6(CH(CH₃)₂)Ph—(CH₂)₂O— | H | H | —CH₂CH₂CH₃ | C₂₈H₃₉NO₂·<br>0.3H₂O | C, 75.91<br>H, 9.01<br>N, 3.16 | C, 75.62<br>H, 8.77<br>N, 3.33 |
| 127 | ± | 8 | 4(CH₃O)Ph(CH₂)₃O— | H | H | —CH₂CH₂CH₃ | C₂₄H₃₁NO₃·<br>0.25H₂O | C, 74.67<br>H, 8.23<br>N, 3.63 | C, 74.50<br>H, 8.06<br>N, 3.78 |
| 128 | ± | 8 | 2(F)Ph(CH₂)₂O— | H | H | —CH₂CH₂CH₃ | C₂₂H₂₆NO₂F·<br>0.55H₂O | C, 72.31<br>H, 7.47<br>N, 3.83 | C, 71.91<br>H, 7.07<br>N, 4.18 |
| 129 | ± | 8 | 3,4-(CH₃O)Ph(CH₂)₂O— | H | H | —CH₂CH₂CH₃ | C₂₄H₃₁NO₄·<br>0.2H₂O | C, 71.86<br>H, 7.89<br>N, 3.49 | C, 71.86<br>H, 7.82<br>N, 3.49 |
| 130 | ± | 8 | 2(CH₃O)Ph(CH₂)₂O— | H | H | —CH₂CH₂CH₃ | C₂₃H₂₉NO₃·<br>0.2H₂O | C, 74.44<br>H, 7.98<br>N, 3.78 | C, 74.22<br>H, 7.70<br>N, 3.44 |
| 131 | ± | 8 | a | H | H | —CH₂CH₂CH₃ | C₂₇H₃₅NO₃·<br>0.4H₂O | C, 75.62<br>H, 8.42<br>N, 3.27 | C, 75.27<br>H, 8.53<br>N, 3.65 |
| 132 | ± | 8 | b | H | H | —CH₂CH₂CH₃ | C₂₅H₃₁NO₃·<br>0.6H₂O | C, 74.26<br>H, 8.03<br>N, 3.49 | C, 73.90<br>H, 7.73<br>N, 3.89 |
| 133 | ± | 8 | 4(F)Ph(CH₂)₂O— | H | H | —CH₂CH₂CH₃ | C₂₂H₂₆NO₂F·<br>0.30H₂O | C, 73.22<br>H, 7.43<br>N, 3.88 | C, 72.94<br>H, 7.44<br>N, 4.26 | a H₃CO-C₆H₄-(cyclopropyl with methyl)-CH₂-O— b H₃CO-C₆H₄-(cyclopropyl)-CH₂-O—

Table 3 shows chemical data for compounds of Formula I wherein X is OCH₃, Y and Z are H, and R₁ is H. The substituents R, G, and R₂ are as indicated in the table below.

TABLE 3

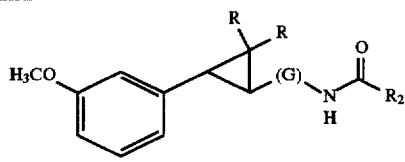

| Ex. No. | Opt. Ism. | Prep. Process | G | R | R₂ | Compound Formula | Elemental analysis Calc'd | Found |
|---|---|---|---|---|---|---|---|---|
| 12 | ± | 12 | CH₂ | F | —CH₂CH₂CH₃ | C₁₅H₁₉F₂NO₂ | C, 63.59<br>H, 6.76<br>N, 4.94 | C, 63.59<br>H, 6.83<br>N, 4.85 |
| 14 | — | 14 | CHCH₃<br>isomer A | H | —CH₂CH₂CH₃ | C₁₆CH₂₃NO₂ | C, 73.53<br>H, 8.87<br>N, 5.36 | C, 73.48<br>H, 8.86<br>N, 5.25 |
| 16 | — | 16 | CH₂CH₂ | H | —CH₂CH₂CH₃ | C₁₆H₂₃NO₂.<br>0.20H₂O | C, 72.53<br>H, 8.90<br>N, 5.29 | C, 72.67<br>H, 8.53<br>N, 5.29 |
| 17 | ± | 17 | CH₂ | CH₃ | —CH₂CH₂CH₃ | C₁₇H₂₅NO₂ | C, 74.14<br>H, 9.15<br>N, 5.09 | C, 73.95<br>H, 9.21<br>N, 5.11 |
| 134 | ± | 12 | CH₂ | F | —CH(CH₃)₂ | C₁₅H₁₉F₂NO₂ | C, 63.59<br>H, 6.76<br>N, 4.94 | C, 63.73<br>H, 6.88<br>N, 4.90 |
| 135 | — | 16 | CH₂CH₂ | H | —CH₂CH₃ | C₁₅H₂₁NO₂ | C, 72.84<br>H, 8.56<br>N, 5.66 | C, 72.56<br>H, 8.53<br>N, 5.35 |
| 136 | — | 14 | CHCH₃<br>isomer B | H | —CH₂CH₂CH₃ | C₁₆H₂₃NO₂ | C, 73.53<br>H, 8.87<br>N, 5.36 | C, 73.24<br>H, 8.93<br>N, 5.30 |
| 137 | — | 14 | CHCH₃<br>isomer A | H | —CH₂CH₃ | C₁₅H₂₁NO₂ | C, 72.84<br>H, 8.56<br>N, 5.66 | C, 72.56<br>H, 8.37<br>N, 5.51 |
| 138 | — | 14 | CHCH₃<br>isomer B | H | —CH₂CH₃ | C₁₅H₂₁NO₂ | C, 72.84<br>H, 8.56<br>N, 5.66 | C, 72.58<br>H, 8.49<br>N, 5.55 |
| 139 | — | 14 | CHCH₃<br>isomer B | H | —CH₃ | C₁₄H₁₉NO₂ | C, 72.07<br>H, 8.21<br>N, 6.00 | C, 71.87<br>H, 8.00<br>N, 5.93 |

Example 140

(Measurement of Melatonergic Binding)

The melatonergic binding of the compounds of Formula I was determined by a modification of the method of Reppert, S. M. et al. (*Neuron*, Volume 13, pages 1177–1185, 1994). Compounds with $IC_{50}$ values of 600 nM or less are termed active. The reagents, membranes, and other parameters used in the assay are described below:

Reagents:

(a) 50 mM Tris buffer containing 12.5 mM $MgCl_2$, and 2 mM EDTA (pH 7.4 at 37° C.).

(b) Wash buffer: 20 mM Tris base containing 2 mM $MgCl_2$ (pH 7.4 at room temperature).

(c) 6-Chloromelatonin ($10^{-5}$M final concentration).

(d) 2-[$^{125}$I]-Iodomelatonin (100 pM final concentration). (Source: NEN) Membrane preparation: The cDNA (human $ML_{1A}$) in pcDNAI was introduced into COS-1 cells by the DEAE-dextran method. Three days later, after media removal, the plates were washed with buffered saline; the cells removed using Hank's balanced salt solution and pelleted. The supernant was discarded and the pellets frozen. For membrane homogenates, the pellets were thawed and resuspended in TME buffer, Tris base, $MgCl_2$, EDTA (pH 7.4 at 37° C.), and supplemented with aprotinin, leupeptin, and phenylmethylsulfonyl fluoride. The cells were homogenized and centrifuged; the resulting pellet resuspended in TME and frozen. At assay, the small aliquot was thawed on ice and resuspended in TME buffer. Incubation: 37° C. for 1 hour. Reaction is terminated by filtration.

Table 4 presents the melatonergic activity for Formula I compounds wherein X is $OCH_3$, R is hydrogen, G is methylene, and the other substituents are as indicated in the table.

TABLE 4

| Ex. No.* | Opt. Ism. | Y | Z | R₁ | R₂ | Binding** |
|---|---|---|---|---|---|---|
| 1 | ± | H | F | H | —CH(CH₃)₂ | ++ |
| 2 | ± | H | H | H | —CH₂CH₂CH₃ | ++++ |
| 3a | + | H | H | H | —CH₂CH₂CH₃ | +++ |
| 3b | − | H | H | H | —CH₂CH₂CH₃ | ++++ |
| 4 | ± | H | I | H | —CH₂CH₂CH₃ | ++++ |
| 5 | − | Br | Br | H | —CH₂CH₂CH₃ | ++++ |
| 6 | ± | H | H | Bn | —CH₂CH₂CH₃ | ++ |
| 9a | + | H | Ph—CC— | H | —CH₂CH₂CH₃ | ++++ |
| 9b | − | H | PhCH₂CH₂— | H | —CH₂CH₂CH₃ | +++ |
| 10 | − | H | CN | H | —CH₂CH₂CH₃ | +++ |
| 11 | − | H | Ph— | H | —CH₂CH₂CH₃ | +++ |
| 13 | − | H | —NHCO(CH₂)₂CH₃ | H | —CH₂CH₂CH₃ | + |
| 18 | ± | H | H | H | —CH₂CH₃ | ++++ |
| 19 | ± | H | H | H | —CH₃ | +++ |
| 20 | ± | H | H | H | —CH₂OCH₃ | +++ |
| 21 | ± | H | H | H | —CH(CH₃)₂ | +++ |
| 22 | − | H | H | H | —CH(CH₃)₂ | +++ |
| 25 | ± | H | H | H | —CH₂CH₂CH₂CH₃ | ++ |
| 27 | ± | Cl | H | H | —CH₂CH₂CH₃ | ++++ |
| 32 | − | H | I | H | —CH₂CH₂CH₃ | ++++ |
| 33 | − | I | H | H | —CH₂CH₂CH₃ | +++ |
| 34 | − | H | 4(CF₃)Ph— | H | —CH₂CH₂CH₃ | +++ |
| 35 | − | H | H | H | —(CH₂)₂CH₂Cl | +++ |
| 36 | − | H | H | H | —CHCH₂CH₂ (cyclic) | ++++ |
| 37 | − | H | H | H | —CHCH₂(CH₂)₂CH₂ (cyclic) | + |
| 39 | − | H | H | H | —NHCH₃ | ++++ |
| 41 | − | H | H | H | —CH₃ | ++++ |
| 42 | − | H | H | H | —CH₂CF₃ | ++++ |

**Binding affinity (nM) at the human melatonin receptor as measured by displacement of the reference compound
(2-[¹²⁵I]-Iodomelatonin) from the receptor. Affinities (IC₅₀) reported fall into the following ranges:
+ 250–600 nM, ++ 40–250 nM, +++ 5–40 nM, and ++++ <5 nM.

Table 5 gives the melatonergic activity for the Formula I compounds wherein R₁ and R are hydrogen, G is methylene and R₂,X,Y, and Z are defined in the table.

TABLE 5

| Ex. No. | Opt. Ism. | X | Y | Z | R₂ | Binding** |
|---|---|---|---|---|---|---|
| 7a | ± | HO— | H | H | —CH₂CH₂CH₃ | + |
| 7b | ± | CH₂=CHCH₂O— | H | H | —CH₂CH₂CH₃ | +++ |
| 8 | ± | (CH₃)₂CHO— | H | H | —CH₂CH₂CH₃ | ++ |
| 15 | ± | HOCH₂CH₂O— | H | H | —CH₂CH₂CH₃ | ++ |
| 44 | ± | F— | H | H | —CH₂CH₂CH₃ | ++ |
| 45 | ± | Ph—(CH₂)₆—O— | H | H | —CH₂CH₂CH₃ | ++ |
| 46 | ± | Ph—(CH₂)₇—O— | H | H | —CH₂CH₂CH₃ | +++ |
| 47 | ± | Ph—C≡C(CH₂)₃—O— | H | H | —CH₂CH₂CH₃ | + |
| 48 | ± | CH₃CH₂O— | H | H | —CH₂CH₂CH₃ | +++ |
| 53 | ± | CH₃(CH₂)₆O— | H | H | —CH₂CH₂CH₃ | ++ |
| 54 | ± | CH₃(CH₂)₇O— | H | H | —CH₂CH₂CH₃ | +++ |
| 55 | ± | CH₃(CH₂)₈O— | H | H | —CH₂CH₂CH₃ | ++ |

TABLE 5-continued

[Structure: X, Y, Z substituted phenyl-cyclopropyl-CH2-NH-C(=O)-R2]

| Ex. No. | Opt. Ism. | X | Y | Z | R₂ | Binding** |
|---|---|---|---|---|---|---|
| 56 | ± | CH₃(CH₂)₉O— | H | H | —CH₂CH₂CH₃ | +++ |
| 57 | ± | CH₃(CH₂)₁₀O— | H | H | —CH₂CH₂CH₃ | +++ |
| 58 | ± | CH₃(CH₂)₁₁O— | H | H | —CH₂CH₂CH₃ | +++ |
| 59 | ± | CH₃(CH₂)₁₅O— | H | H | —CH₂CH₂CH₃ | + |
| 60 | ± | Ph—CH₂CH₂O— | H | H | —CH₂CH₂CH₃ | +++ |
| 61 | ± | (CH₃)₂CHCH₂O— | H | H | —CH₂CH₂CH₃ | + |
| 62 | ± | 3(CH₃O)Ph(CH₂)₂O— | H | H | —CH₂CH₂CH₃ | +++ |
| 63 | ± | 4-Pyridyl(CH₂)₃O— | H | H | —CH₂CH₂CH₃ | ++ |
| 64 | − | CF₃O | H | H | —CH₂CH₂CH₃ | +++ |
| 65 | − | F | H | H | —CH(CH₃)₂ | + |
| 66 | + | F | H | Br | —CH₂CH₂CH₃ | +++ |
| 69 | − | CF₃O | I | H | —CH₂CH₂CH₃ | +++ |
| 70 | + | F | H | I | —CH₂CH₂CH₃ | ++ |
| 71 | − | F | I | H | —CH₂CH₂CH₃ | ++ |
| 72 | + | CF₃O | H | Br | —CH₂CH₂CH₃ | ++ |
| 73 | ± | Br | H | H | —CH₂CH₂CH₃ | +++ |
| 75 | ± | CH₃ | H | H | —CH₂CH₂CH₃ | +++ |
| 78 | ± | CH₃ | H | H | —CH₃ | ++ |
| 79 | − | HO | H | H | —CH₂CH₂CH₃ | ++ |
| 80 | ± | Cl | H | H | —CH₂CH₂CH₃ | +++ |
| 84 | − | 3(CH₃O)Ph(CH₂)₃O— | H | H | —CH₂CH₂CH₃ | ++++ |
| 87 | ± | F | H | F | —CH₂CH₂CH₃ | ++ |
| 89 | − | CF₂CF₃ | H | H | —CH₂CH₂CH₃ | ++ |
| 90 | − | H | H | H | —CH₂CH₂CH₃ | ++ |
| 93 | − | 3(CH₃O)Ph(CH₂)₃O— | H | I | —CH₂CH₂CH₃ | +++ |
| 94 | ± | F(CH₂)₃O— | H | H | —CH₂CH₂CH₃ | ++ |
| 95 | ± | Ph(CH₂)₃O— | H | H | —CH₂CH₂CH₃ | +++ |
| 96 | ± | PhO(CH₂)₃O— | H | H | —CH₂CH₂CH₃ | +++ |
| 98 | ± | 1-Pyrryl(CH₂)₃O— | H | H | —CH₂CH₂CH₃ | +++ |
| 99 | ± | (CH₃)₂C=CH(CH₂)₂—C(CH₃)=CHCH₂O— | H | H | —CH₂CH₂CH₃ | +++ |
| 100 | ± | (CH₃)₂C(CH₂)₄O— | H | H | —CH₂CH₂CH₃ | +++ |
| 103 | ± | (CH₃)₂C=CH—(CH₂)₂C(CH₃)=CH(CH₂)₂C(CH₃)=CHCH₂O— | H | H | —CH₂CH₂CH₃ | ++++ |
| 105 | ± | CH₂=CH(CH₂)₃O— | H | H | —CH₂CH₂CH₃ | +++ |
| 106 | ± | (CH₃)₂C=CH(CH₂)₂O— | H | H | —CH₂CH₂CH₃ | +++ |
| 107 | ± | NC(CH₃)₂C(CH₂)₄O— | H | H | —CH₂CH₂CH₃ | ++ |
| 108 | ± | CH₃O₂C(CH₂)₃O— | H | H | —CH₂CH₂CH₃ | ++ |
| 110 | ± | Ph(CH₂)₉O— | H | H | —CH₂CH₂CH₃ | ++++ |
| 111 | ± | CD₃O— | H | H | —CH₂CH₂CH₃ | ++++ |
| 114 | ± | CH₂CH₃ | H | H | —CH₂CH₂CH₃ | +++ |
| 116 | ± | cyclohexyl(CH₂)₄O— | H | H | —CH₂CH₂CH₃ | +++ |
| 120 | ± | cyclopentyl(CH₂)₃O— | H | H | —CH₂CH₂CH₃ | ++++ |
| 121 | ± | (CH₃)₃CCH₂CH—(CH₃)CH₂CH₂O— | H | H | —CH₂CH₂CH₃ | +++ |
| 122 | ± | HC≡CC(CH₃)=CH—CH₂O— | H | H | —CH₂CH₂CH₃ | +++ |
| 123 | ± | 3(CF₃)Ph(CH₂)₂O— | H | H | —CH₂CH₂CH₃ | ++++ |
| 125 | ± | 3(F)Ph(CH₂)₂O— | H | H | —CH₂CH₂CH₃ | +++ |
| 127 | ± | 4(CH₃O)Ph(CH₂)₃O— | H | H | —CH₂CH₂CH₃ | +++ |
| 128 | ± | 2(F)Ph(CH₂)₂O— | H | H | —CH₂CH₂CH₃ | +++ |
| 131 | ± | a | H | H | —CH₂CH₂CH₃ | +++ |
| 132 | ± | b | H | H | —CH₂CH₂CH₃ | ++++ |

**Binding affinity (nM) at the human melatonin receptor as measured by displacement of the reference compound (2-[$^{125}$I]-Iodomelatonin) from the receptor. Affinities (IC$_{50}$) reported fall into the following ranges:
+ 250–600 nM, ++ 40–250 nM, +++ 5–40 nM, and ++++ <5 nM.

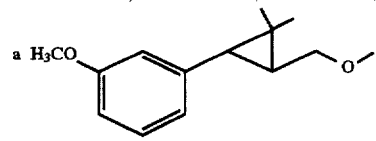

a

TABLE 5-continued

| Ex. No. | Opt. Ism. | X | Y | Z | R₂ | Binding** |
|---|---|---|---|---|---|---|
| b | | H₃CO 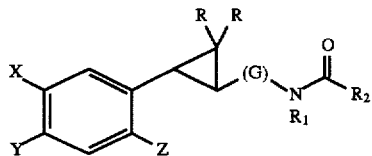 | | | | |

Table 6 presents the melatonergic activity for compounds of Formula I wherein X is OCH₃, Y and Z are H, and R₁ is H. The substituents R, G, and R₂ are as indicated in the table below.

TABLE 6

| Ex. No. | Opt. Ism. | G | R | R₂ | Binding** |
|---|---|---|---|---|---|
| 12 | +/− | CH₂ | F | —CH₂CH₂CH₃ | +++ |
| 14 | − | CHMe isomer A | H | —CH₂CH₂CH₃ | ++ |
| 16 | − | CH₂CH₂ | H | —CH₂CH₂CH₃ | + |
| 17 | +/− | CH₂ | CH₃ | —CH₂CH₂CH₃ | + |
| 134 | +/− | CH₂ | F | —CH(CH₃)₂ | ++ |
| 136 | − | CHMe isomer B | H | —CH₂CH₂CH₃ | +++ |

**Binding affinity (nM) at the human melatonin receptor as measured by displacement of the reference compound (2-[$^{125}$I]-Iodomelatonin) from the receptor. Affinities (IC$_{50}$) reported fall into the following ranges:
+ 250–600 nM, ++ 40–250 nM, +++ 5–40 nM, and ++++ <5 nM.

Reasonable variations, such as those which would occur to a skilled artisan, can be made herein without departing from the scope of the invention.

We claim:

1. A melatonergic compound of Formula I (I)

wherein:
X is halogen, hydrogen, $C_{1-4}$ alkyl or OR₅, wherein R₅ is hydrogen, $C_{1-4}$ perfluoroalkyl, $C_{1-4}$ fluoroalkyl, $C_{1-4}$ perdeuteroalkyl, $C_{1-20}$ alkyl, $C_{4-20}$ alkcycloalkyl, $C_{2-20}$ carbonitriloalkyl, $C_{3-22}$ carboalkoxyalkyl, $C_{3-20}$ alkenyl, $C_{3-20}$ alkynyl, $C_{9-20}$ aralkyl, $C_{9-20}$ aralkenyl, $C_{9-20}$ aralkynyl, $C_{2-20}$ hydroxyalkyl or $C_{8-20}$ aryloxyalkyl Y is hydrogen or halogen;

Z is hydrogen, halogen, cyano, aryl, $C_{7-20}$ aralkyl, $C_{8-20}$ aralkynyl, or $C_{2-20}$ alkamido;

R, in both cases, is hydrogen, halogen, or $C_{1-4}$ alkyl;

G is a divalent methylene, ethylene, or $C_{1-4}$ alkmethylene moiety;

R₁ is hydrogen, $C_{1-4}$ alkyl or benzyl; and

R₂ is $C_{1-6}$ alkyl, $C_{2-6}$ alkenyl, $C_{3-6}$ cycloalkyl, $C_{2-4}$ alkoxyalkyl, $C_{1-4}$ trifluoromethylalkyl or $C_{2-8}$ alkylthioalkyl.

2. The compound of claim 1 wherein R₁ is hydrogen; R₂ is $C_{1-6}$ alkyl, $C_{2-6}$ alkenyl or $C_{3-6}$ cycloalkyl; Y and Z are hydrogen and X is methoxy.

3. The compound of claim 2 selected from the group consisting of:

(trans)-N-[[2-(3-Methoxyphenyl)cyclopropyl]methyl] butanamide;

(−)-(trans)-N-[[2-(3-Methoxyphenyl)cyclopropyl]methyl] butanamide;

(trans)-N-[[2-(3-Methoxyphenyl)cyclopropyl]methyl] propanamide;

(+)-(trans )-N-[[2-(3-Methoxyphenyl)cyclopropyl]-methyl] butanamide;

(trans)-N-[[2-(3-Methoxyphenyl)cyclopropyl]methyl] acetamide; and (−)-(trans)-N-[[2-(3-Methoxyphenyl)cyclopropyl]methyl]-2-methylpropanamide.

4. The compound of claim 2 wherein one or more of X, Y and Z is halogen.

5. The compound of claim 4 selected from the group consisting of:

(trans)-N-[[2-(4-Chloro-3-methoxyphenyl)cyclopropyl] methyl] butanamide;

(trans)-N-[[2-(2-Bromo-5-methoxyphenyl)cyclopropyl] methyl] butanamide;

(trans)-N-[[2-(2,4-Dibromo-5-methoxyphenyl)-cyclopropyl]methyl] butanamide;

(trans)-N-[[2-(2-Iodo-5-methoxyphenyl)cyclopropyl] methyl] butanamide; and (−)-(trans)-N-[[2-(2-Iodo-5-methoxyphenyl)cyclopropyl] methyl] butanamide.

6. The compound of claim 1 wherein R₁ is hydrogen, R₂ is alkyl, alkenyl or cycloalkyl, X and Z are hydrogen and R₅ is $C_{2-20}$ alkyl, $C_{9-20}$ aralkyl or $C_{3-20}$ alkenyl.

7. The compound of claim 6 selected from the group consisting of:

(trans)-N-[[2-(3-[(Ethoxyphenyl)cyclopropyl]methyl] butanamide;

(trans)-N-[[2-[(3-Octyloxy)phenyl]cyclopropyl]methyl] butanamide;

(trans)-N-[[2-[(3-Decyloxy)phenyl]cyclopropyl]methyl] butanamide;

(trans)-N-[[2-[(3-Undecyloxy)phenyl]cyclopropyl]methyl] butanamide;

(trans)-N-[[2-[(3-Dodecyloxy)phenyl]cyclopropyl]methyl] butanamide;

(trans)-N-[[2-[3-(Heptyloxy)phenyl]cyclopropyl]methyl] butanamide;

(trans)-N-[[2-[3-(Nonyloxy)phenyl]cyclopropyl]methyl] butanamide;

(trans)-N-[[2-[3-(2-Propenyloxy)phenyl]cyclopropyl methyl] butanamide;

(trans)-N-[[2-[3-(6-Phenylhexyl)oxy]phenyl]cyclopropyl methyl] butanamide;

(trans)-N-[[2-[3-[(7-Phenylheptyl)oxy]phenyl]cyclopropyl methyl] butanamide;

(trans)-N-[[2-[3-[(2-Phenylethyl)oxy]phenyl]cyclopropyl methyl] butanamide; and (trans)-N-[[2-[3-[3-(3-Methoxyphenyl)propoxy]phenyl] cyclopropyl]methyl] butanamide.

8. A method of treating a circadian rhythm-related disorder in a patient in need of such treatment comprising administering to said patient a therapeutic amount of a compound of claim 1.

9. A pharmaceutical composition for treating circadian rhythm-related disorders comprising a suitable amount of a pharmaceutically acceptable carrier and a therapeutic amount of a compound of claim 1.

10. A radioligand comprising a radiochemically substituted compound of claim 1.

11. The compound of claim 1, (−)-(trans)-N-[[2-(2-Iodo-5-methoxyphenyl)cyclopropyl]methyl] butanamide.

12. The compound of claim 1, (−)-(trans)-N-[[2-(3-methoxyphenyl)cyclopropyl]methyl] butanamide.

13. The compound of claim 1, (trans)-N-[[2-(3-methoxyphenyl)cyclopropyl]methyl] propanamide.

14. The compound of claim 1, (trans)-N-[[2-(3-methoxyphenyl)cyclopropyl]methyl] propanamide.

15. The compound of claim 1, (trans)-N-[[2-(4-Chloro-3-methoxyphenyl)cyclopropyl]methyl] butanamide.

16. The compound of claim 1, (trans)-N-[[3-(3-Methoxyphenyl)-2,2-difluoro-1-cycloprop-1-yl]methyl] butanamide.

17. The compound of claim 1, (trans)-N-[[3-(3-Methoxyphenyl)-2,2-difluoro-1-cycloprop-1-yl]methyl]-2-methylpropanamide.

18. The compound of claim 1, (−)-(trans)-N-[[2-(5-Fluoro-2-iodophenyl)cycloprop-1-yl]methyl]butanamide.

19. The compound of claim 1 selected from the group consisting of:

(trans)-N-[[2-(3-Chlorophenyl)cycloprop-1-yl]methyl] butanamide;

(trans)-N-[[2-(3-Bromophenyl)cycloprop-1-yl]methyl] butanamide;

(−)-(trans)-N-[[2-(3-Fluorophenyl)cyclopropyl]methyl] butanamide;

(trans)-N-[[2-(2,5-Difluorophenyl)cycloprop-1-yl]methyl] butanamide;

(trans)-N-[[2-(2-Bromo-5-fluorophenyl)cycloprop-1-yl] methyl] butanamide;

(trans)-N-[[2-(3-Methylphenyl)cycloprop-1-yl]methyl] butanamide;

(trans)-N-[2-[(3-Ethylphenyl)cycloprop-1-yl]methyl] butanamide; and (trans)-N-[[2-[3-(Trifluoromethoxy)phenyl] cycloprop-1-yl] methyl] butanamide.

* * * * *